(12) United States Patent
Ueda et al.

(10) Patent No.: US 10,850,086 B2
(45) Date of Patent: Dec. 1, 2020

(54) MEDICAL CONNECTOR

(71) Applicant: TERUMO KABUSHIKI KAISHA, Tokyo (JP)

(72) Inventors: Yasuhiro Ueda, Kofu (JP); Takeshi Toyama, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 200 days.

(21) Appl. No.: 15/716,290

(22) Filed: Sep. 26, 2017

(65) Prior Publication Data

US 2018/0015276 A1  Jan. 18, 2018

Related U.S. Application Data

(63) Continuation of application No. PCT/JP2016/001761, filed on Mar. 25, 2016.

(30) Foreign Application Priority Data

Mar. 26, 2015 (JP) ................................. 2015-063685

(51) Int. Cl.
*A61M 39/10* (2006.01)
*A61J 1/14* (2006.01)

(52) U.S. Cl.
CPC ............ *A61M 39/1011* (2013.01); *A61J 1/14* (2013.01); *A61M 2039/1044* (2013.01)

(58) Field of Classification Search
CPC ........ A61M 39/1011; A61M 2039/1044; A61J 1/14
See application file for complete search history.

(56) References Cited

U.S. PATENT DOCUMENTS

| 5,934,709 | A | 8/1999 | Morrison | |
|---|---|---|---|---|
| 2003/0144647 | A1* | 7/2003 | Miyahara | A61M 39/162 604/523 |
| 2011/0095528 | A1* | 4/2011 | Forberg | A61M 39/10 285/374 |
| 2014/0191501 | A1* | 7/2014 | Brugger | F16L 35/00 285/120.1 |
| 2014/0207118 | A1* | 7/2014 | Tsoukalis | A61M 39/14 604/535 |

(Continued)

FOREIGN PATENT DOCUMENTS

| JP | S50-052515 | 5/1975 |
|---|---|---|
| JP | H07-016097 | 3/1995 |

(Continued)

OTHER PUBLICATIONS

International Search Report and Written Opinion received in International Application No. PCT/JP2016/001761 dated Jun. 14, 2016.

(Continued)

*Primary Examiner* — Lauren P Farrar
(74) *Attorney, Agent, or Firm* — Foley & Lardner LLP

(57) ABSTRACT

A medical connector includes a male connector portion, an engagement portion, and a locking portion that slides on the engagement portion to set a locked state in which the engagement portion is inhibited from being pulled out of another medical connector when the male connector portion is inserted into a female connector portion of the other medical connector.

12 Claims, 26 Drawing Sheets

(56) References Cited

U.S. PATENT DOCUMENTS

2015/0105753 A1* 4/2015 Okiyama ............ A61M 39/045
604/535

FOREIGN PATENT DOCUMENTS

| JP | 2004-000483 A | 1/2004 |
| JP | 2006-223583 | 8/2006 |
| JP | 2008-173343 | 7/2008 |
| WO | WO-2012/128321 A1 | 9/2012 |
| WO | WO-2013/136889 A1 | 9/2013 |

OTHER PUBLICATIONS

Japanese Office Action dated Dec. 3, 2019 for corresponding Application No. 2017-507509.

* cited by examiner

MEDICAL CONNECTOR

CROSS-REFERENCE TO RELATED APPLICATIONS

The present application is a bypass continuation of PCT Application No. PCT/JP2016/001761, filed on Mar. 25, 2016, which claims priority to Japanese application No. 2015-063685, filed on Mar. 26, 2015. The contents of these applications are hereby incorporated by reference in their entireties.

BACKGROUND

The present application relates to a medical connector including a male connector portion and an engagement portion and particularly to a technique of suppressing an unintended displacement of the other medical connector while ensuring the ease of a connection operation with respect to the other medical connector.

Hitherto, a medical connector for connecting passages has been used in an infusion set for injecting a liquid such as a medical liquid into a living body of a patient or other medical instruments. In general, a connection of such a medical connector is performed in such a manner that a male connector portion provided at one connector is inserted into a female connector portion provided at the other connector. Also, an engagement portion is generally provided between the connectors in order to prevent an unintended separation of the connector. For example, in a luer locking type connector, a screw is used as the engagement portion, but since two steps of connection operations are necessary at the time of the connection such that the male connector portion is inserted into the female connector portion and is fixed by the screw, the connection operation is complex.

In order to solve such a problem, for example, as disclosed in JP 2004-483 A and WO 2012/128321 A1, a method of using a plurality of claws as the engagement portion is known. A medical connector disclosed in JP 2004-483 A and WO 2012/128321 A1 includes a male connector portion and a plurality of claws. Here, when the male connector portion is inserted into a female connector portion of the other medical connector, the plurality of claws climbs over a stepped portion formed at the other medical connector while being elastically deformed and is restored after the climbing, thereby preventing the claws from being pulled out of the stepped portion. According to such a configuration, since it is possible to connect the connectors to each other just by inserting the male connector portion into the female connector portion, it is possible to easily perform a connection operation.

SUMMARY

However, in the medical connector disclosed in JP 2004-483 A and WO 2012/128321 A1, there is a possibility that an unintended displacement of the other medical connector may be caused when the claws climb over the stepped portion while being elastically deformed at the time of the connection to the other medical connector.

That is, when the medical connector (hereinafter, referred to as a first connector) disclosed in, for example, JP 2004-483 A and WO 2012/128321 A1 is held by a right hand, the other medical connector (hereinafter, referred to as a second connector) is held by a left hand, and the first connector is connected to the second connector, the second connector should be pressed back with the same force as a force pressed from the first connector in order to immovably connect the second connector.

Incidentally, when the claws climb over the stepped portion of the second connector, the force pressed from the first connector and applied to the second connector abruptly decreases. At this time, there is a possibility that the second connector may be displaced toward the first connector (that is, an unintended displacement may be caused) due to the force pressing the second connector toward the first connector by the left hand. If the second connector is displaced, for example, when the male connector portion of the first connector disposed at a distal end of an infusion set is connected to the female connector portion disposed at a catheter hub of an indwelling needle serving as the second connector, a problem arises in that a distal end position of the catheter is displaced and is separated from a blood vessel.

Embodiments described herein have been made in view of the above-described circumstances and an object of the certain embodiments is to provide a medical connector capable of suppressing an unintended displacement of the other medical connector while ensuring the ease of a connection operation with respect to the other medical connector.

According to one embodiment, a medical connector includes a male connector portion and an engagement portion, including: a locking portion which slides on the engagement portion to set a locked state where the engagement portion is not pulled out of the other medical connector when the male connector portion is inserted into a female connector portion of the other medical connector.

In the above medical connector, the engagement portion includes a plurality of claws, and the locking portion includes a cylinder wall which surrounds the plurality of claws and a locking protrusion which is formed at an inner peripheral surface of the cylinder wall.

In one aspect, when the male connector portion is inserted into the female connector portion of the other medical connector, the cylinder wall slides while being pressed by the other medical connector and the locking protrusion presses the plurality of claws to elastically deform the claws, so that the locking portion sets a locked state where the plurality of claws are not able to be pulled out of the other medical connector.

In one aspect, the engagement portion includes a plurality of claws and outer peripheral protrusions which are formed at outer peripheral surfaces of the plurality of claws, and the locking portion includes a cylinder wall which surrounds the plurality of claws.

In one aspect, when the male connector portion is inserted into the female connector portion of the other medical connector, the male connector portion slides while coming into contact with the female connector portion and the cylinder wall presses the outer peripheral protrusions to elastically deform the plurality of claws, so that the locking portion sets a locked state where the plurality of claws are not able to be pulled out of the other medical connector.

In one aspect, the medical connector further includes: a fitting wall which is connected to proximal end portions of the plurality of claws, wherein a fitting wall side fitting portion and a cylinder wall side fitting portion which are fitted to each other to prevent the cylinder wall from sliding toward the other medical connector when the cylinder wall sets the plurality of claws in the locked state are provided between the fitting wall and the cylinder wall.

In one aspect, the cylinder wall includes an operation portion formed at an outer peripheral surface of the cylinder wall, and when the operation portion is pressed, the fitting between the fitting wall side fitting portion and the cylinder wall side fitting portion is released.

In one aspect, the medical connector further includes: a complete locking visual check portion which protrudes from a proximal end surface of the cylinder wall toward a proximal end side and is visible from the outside of the cylinder wall in the radial direction when the locking portion slides so that the plurality of claws are set to the locked state.

In one aspect, the cylinder wall of the locking portion includes a rotation regulation portion which prohibits a rotation of the female connector portion of the other medical connector relative to the cylinder wall.

In one aspect, the male connector portion includes a sealing portion which seals an outer surface of the female connector portion.

According to certain embodiments, when the male connector portion is inserted into the female connector portion of the other medical connector, the locking portion slides on the engagement portion and a locked state where the engagement portion cannot be pulled out of the other medical connector can be set by the locking portion sliding in this way. Thus, it is possible to connect the connectors to each other just by inserting the male connector portion into the female connector portion of the other medical connector. Further, because a state in which the engagement portion cannot be pulled out of the other medical connector can be set by the sliding of the locking portion, it is possible to eliminate or reduce the necessity that the engagement portion climbs over the stepped portion of the other medical connector to set the state where the engagement portion cannot be pulled out.

Thus, it is possible to provide a medical connector capable of suppressing an unintended displacement of the other medical connector while ensuring the ease of a connection operation with respect to the other medical connector.

BRIEF DESCRIPTION OF THE DRAWINGS

FIG. 1A is a longitudinal sectional view, FIG. 1B is a cross sectional view, and FIG. 1C is a perspective view.

FIG. 4A is a longitudinal sectional view and FIG. 4B is a cross sectional view.

FIG. 5A is a longitudinal sectional view and FIG. 5B is a cross sectional view.

FIG. 6A is a longitudinal sectional view, FIG. 6B is a cross sectional view, and FIG. 6C is a perspective view.

FIG. 7A is a longitudinal sectional view and FIG. 7B is across sectional view.

FIG. 8A is a longitudinal sectional view and FIG. 8B is a cross sectional view.

FIG. 9A is a longitudinal sectional view and FIG. 9B is a cross sectional view.

FIG. 10A is a longitudinal sectional view, FIG. 10B is a cross-sectional view taken along the line A-A of FIG. 10A, and FIG. 10C is a perspective view.

FIG. 13A is a longitudinal sectional view and FIG. 13B is a cross-sectional view taken along the line A-A of FIG. 13A.

FIG. 14A is a longitudinal sectional view and FIG. 14B is a cross-sectional view taken along the line A-A of FIG. 14A.

FIG. 15A is a longitudinal sectional view, FIG. 15B is a cross sectional view, and FIG. 15C is a perspective view.

FIG. 18A is a longitudinal sectional view and FIG. 18B is a cross sectional view.

FIG. 19A is a longitudinal sectional view and FIG. 19B is a cross sectional view.

FIG. 20A is a longitudinal sectional view, FIG. 20B is a cross sectional view, and FIG. 20C is a perspective view.

FIG. 23A is a longitudinal sectional view and FIG. 23B is a cross sectional view.

FIG. 24A is a longitudinal sectional view and FIG. 24B is a cross sectional view.

FIG. 26A illustrates a connector separation state and FIG. 26B illustrates a complete locking state.

DETAILED DESCRIPTION

Figure 1A:
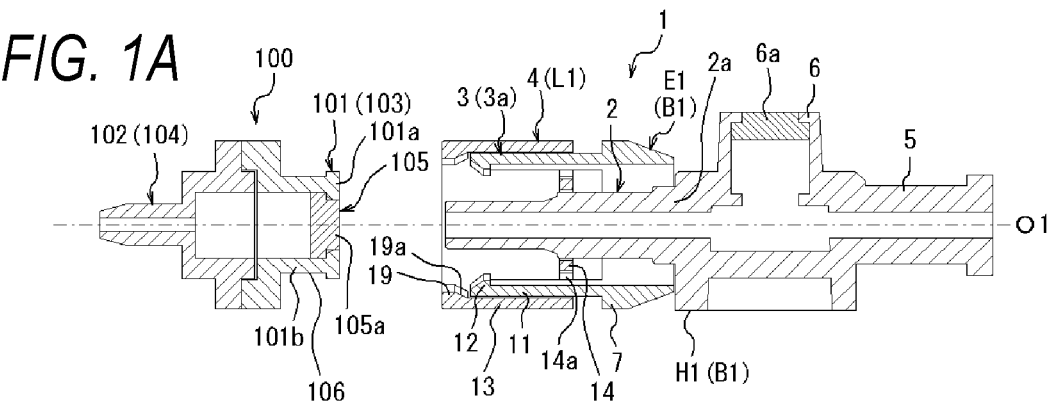
FIGS. 1A-1C illustrate a state at the time of separation between a medical connector according to an embodiment of the invention and another medical connector, where

Hereinafter, embodiments of a medical connector 1 will be described in detail with reference to FIGS. 1A to 9B.

In addition, in the present specification, a distal end side means a distal end side (for example, a left side in FIG. 1A) of a male connector portion 2 in a direction along a center axis O1 of the male connector portion 2 of the medical connector 1 and a proximal end side means the opposite side.

As illustrated in FIGS. 1A to 3, the medical connector 1 according to this embodiment includes the male connector portion 2, an engagement portion 3, and a locking portion 4 and is connectable to the other medical connector 100. In this example, the male connector portion 2 is integrated with a housing H1. Further, in this example, the engagement portion 3 is formed at an engagement member E1 fixed to the housing H1 and is formed as a plurality of (in this example, two) claws 3a. Further, in this example, the locking portion 4 is formed as a locking member L1 attached to the housing H1 to be slidable. The medical connector 1 according to this embodiment includes a connector body B1 including the housing H1 and the engagement member E1 and the locking member L1 attached to the connector body B1 to be slidable in the direction of the axis O1 of the male connector portion 2. The housing H1, the engagement member E1, and the locking member L1 can be formed of, for example, a synthetic resin.

The housing H1 is provided with a female connector portion 5 and a mixed injection port portion 6. An opening portion of the mixed injection port portion 6 is provided with a valve body 6a which opens the opening portion to form a passage when each of male connector portions of various medical connectors is inserted thereinto and closes the opening portion when such male connector portions are not inserted thereinto.

In addition, in this example, the medical connector 1 is formed as a T-port connector including the female connector portion 5 and the mixed injection port portion 6 along with the male connector portion 2, but the invention is not limited to such a configuration. For example, the medical connector 1 can be formed as a three-way stopcock further including a passage switching structure or can be formed as a male connector directly attached to an end portion of a tube connected to an infusion container.

The engagement member E1 includes a cylindrical fitting wall 7 which is connected to proximal end portions of the plurality of claws 3a. A proximal end side end portion of the fitting wall 7 is provided with a pair of protrusions 8 which protrudes toward the inner peripheral side. The pair of protrusions 8 is fitted to a proximal end portion 2a of the male connector portion 2 of the housing H1, so that the engagement member E1 is fixed to the housing H1.

Specifically, each of the pair of protrusions 8 includes two protrusions 8a and the totally four protrusions 8a are fitted to the totally four concave portions 9 formed at the proximal end portion 2a of the male connector portion 2. A proximal flange 10 which defines a part of four concave portions 9 is formed in the vicinity of the proximal end portion 2a of the male connector portion 2 and a distal end surface of the proximal flange 10 is formed as a tapered surface 10a which increases in diameter toward the proximal end side. Thus, since the pair of protrusions 8 is pressed against the tapered surface 10a of the proximal flange 10 at the time of fixing the engagement member E1 to the housing H1, it is possible to fit the pair of protrusions 8 to the proximal end portion 2a of the male connector portion 2 while elastically deforming the pair of protrusions to climb over the proximal flange 10.

Further, the fitting wall 7 is provided with a plurality of (in this example, two) fitting wall side fitting portions 7a which are fittable to a plurality of (in this example, two) cylinder wall side fitting portions 17 which will be described later and are formed at a locking member L1. In this example, the fitting wall side fitting portion 7a is formed as an opening portion.

Each of the plurality of claws 3a includes a plate piece 11 which extends along the axis O1 and has a circular-arc cross-section and an engagement protrusion 12 which is formed at a distal end portion of the plate piece 11 to protrude toward the inner peripheral side. A distal end surface of the engagement protrusion 12 of each of the plurality of claws 3a is formed as a tapered surface 12a of which a protruding width of the engagement protrusion 12 decreases toward the distal end side.

The locking member L1 includes a cylinder wall 13. A proximal end side end portion of the cylinder wall 13 is provided with a pair of protrusions 14 which protrudes toward the inner peripheral side. The pair of protrusions 14 is provided with insertion holes 14a into which the plurality of claws 3a are inserted. Further, the pair of protrusions 14 is attached to an intermediate portion of the male connector portion 2 of the housing H1 in the direction of the axis O1 to be slidable.

Specifically, each of the pair of protrusions 14 includes two protrusions 14b and the totally four protrusions 14b are disposed inside the totally four groove portions 15 formed at the intermediate portion of the male connector portion 2 in the direction of the axis O1. As a result, the locking member L1 is attached to the male connector portion 2 of the housing H1 to be slidable.

A distal flange 16 which defines apart of the groove portion 15 is formed at the distal end side of four groove portions 15 of the male connector portion 2 and a distal end surface of the distal flange 16 is formed as a tapered surface 16a which increases in diameter toward the proximal end side. Thus, since the pair of protrusions 14 is pressed against the tapered surface 16a of the distal flange 16 at the time of attaching the locking member L1 to the housing H1, it is possible to attach the pair of protrusions 14 to the intermediate portion of the male connector portion 2 in the direction of the axis O1 while elastically deforming the pair of protrusions to climb over the distal flange 16. Additionally, since the pair of protrusions 14 is held by the distal flange 16 after the locking member L1 is attached to the housing H1 in this way, it is possible to prevent the locking member L1 from being separated from the housing H1.

Further, the proximal end side of the cylinder wall 13 is provided with a plurality of (in this example, two) cylinder wall side fitting portions 17 which are fittable to a plurality of (in this example, two) fitting wall side fitting portions 7a of the engagement member E1. In this example, the cylinder wall side fitting portion 17 includes a fitting protrusion 17a which is fittable to the fitting wall side fitting portion 7a formed as an opening portion.

An outer peripheral surface of the cylinder wall 13 is provided with an operation portion 18 and the fitting between the fitting wall side fitting portion 7a and the cylinder wall side fitting portion 17 is released by the pressing of the operation portion 18. In this example, the cylinder wall side fitting portion 17 is fitted to the fitting wall side fitting portion 7a from the inner peripheral side and the cylinder wall side fitting portion 17 is elastically deformed toward the inner peripheral side by the pressing of the operation portion 18. In this example, two sets of the operation portion 18, the fitting wall side fitting portion 7a, and the cylinder wall side fitting portion 17 are provided at positions facing each other with the axis O1 interposed therebetween.

The inner peripheral surface of the cylinder wall 13 is provided with a locking protrusion 19 which presses the plurality of claws 3a so that the claws are elastically deformed toward the inner peripheral side when the cylinder wall 13 is slid toward the proximal end side with respect to the plurality of claws 3a. In this example, the locking protrusion 19 is formed as a plurality of (in this example, two) protrusions corresponding to the plurality of claws 3a. A proximal end surface of the locking protrusion 19 is formed as a tapered surface 19a of which a protruding width of the locking protrusion 19 increases toward the distal end side.

Figure 1B:
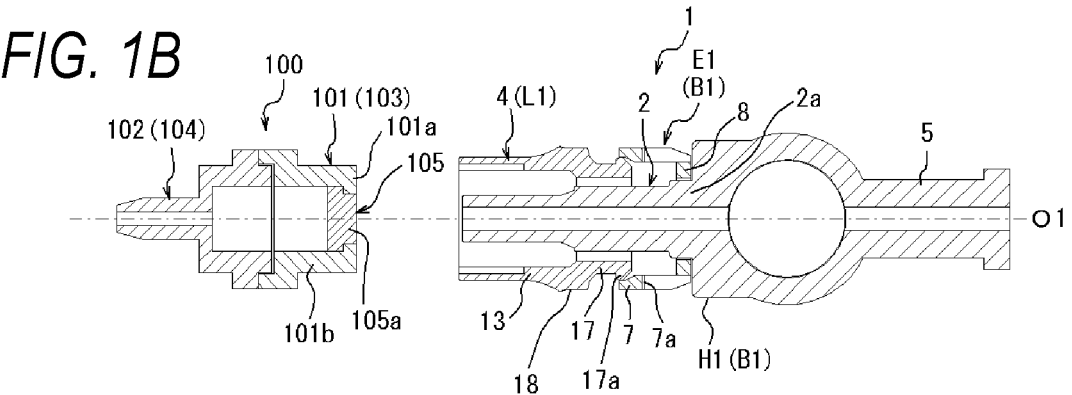
Figure 1C:
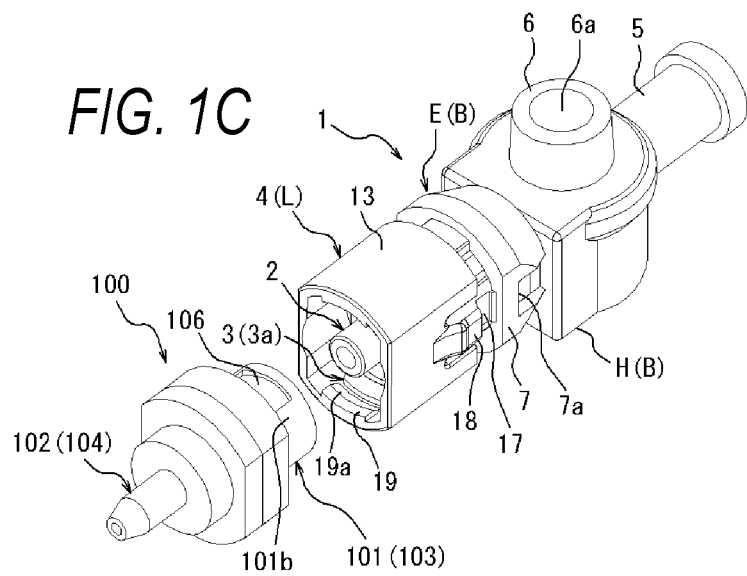
Figure 2:
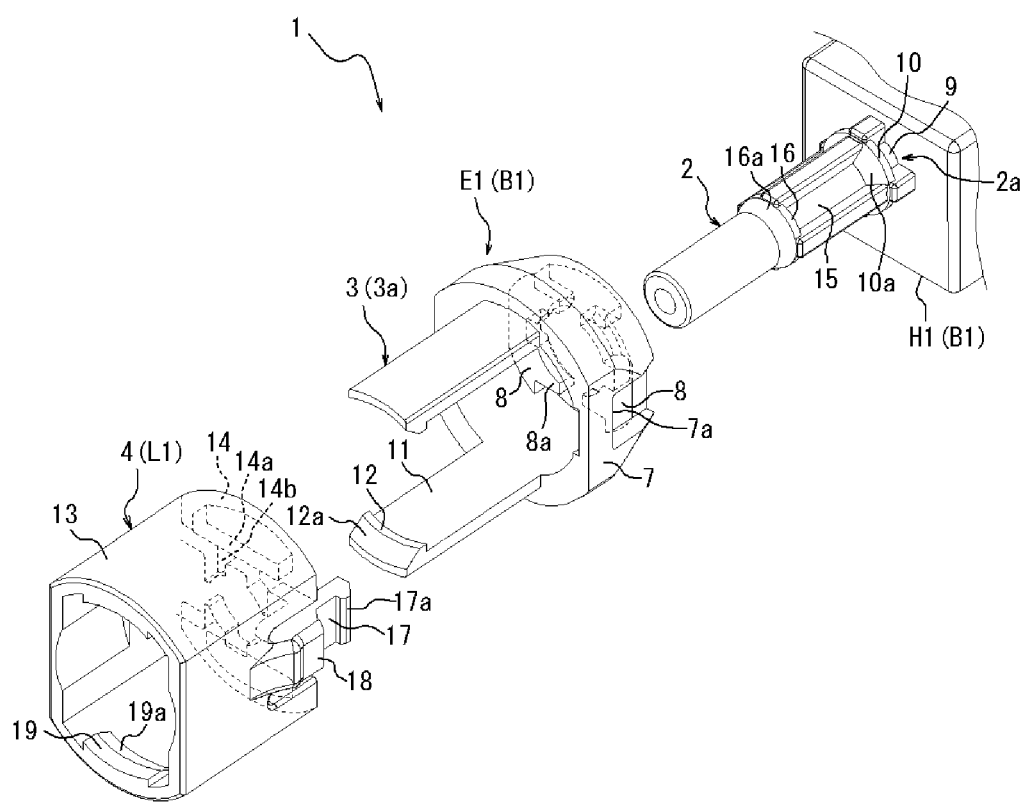
FIG. 2 is an exploded perspective view of the medical connector illustrated in FIG. 1.
Figure 3:
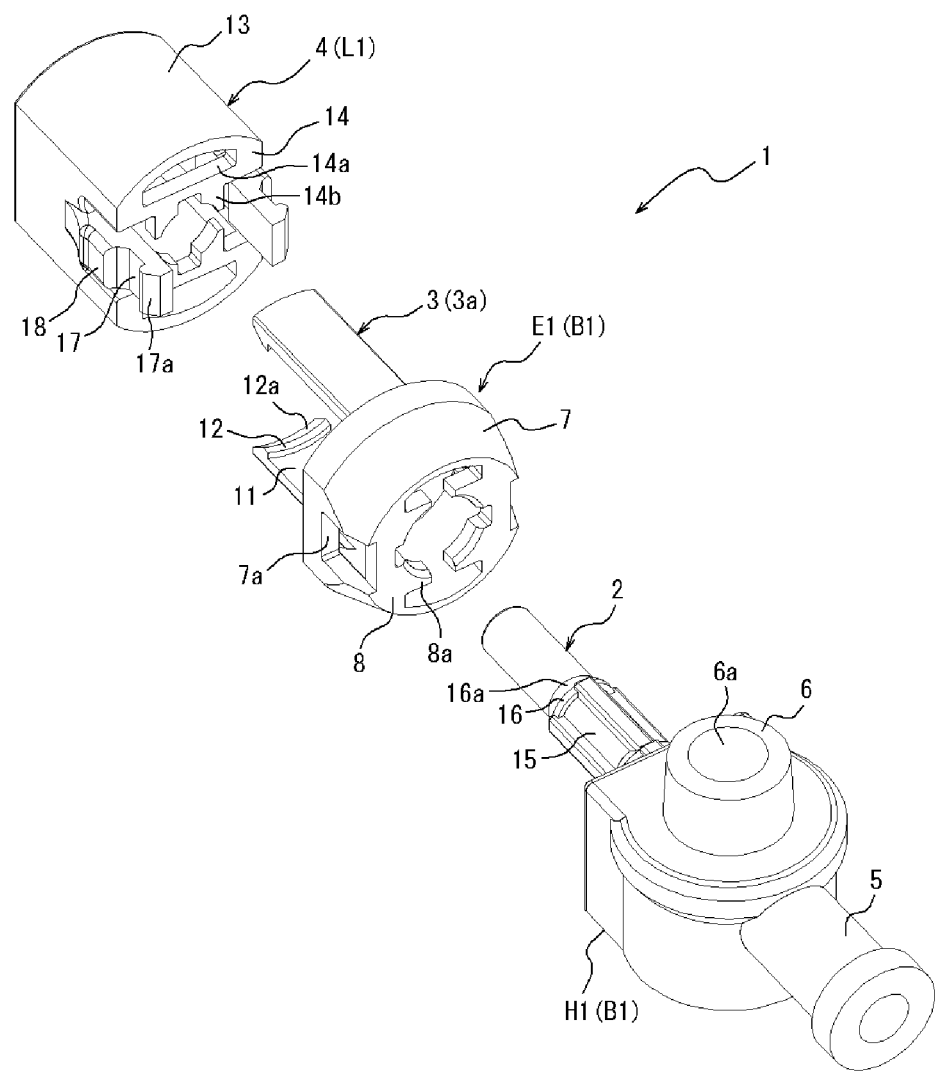
FIG. 3 is an exploded perspective view in which the medical connector illustrated in FIG. 1 is viewed from a different angle.

As illustrated in FIGS. 1A-1C, the other medical connector 100 includes a female connector portion 101. Further, in this example, the other medical connector 100 also includes a male connector portion 102. The male connector portion 102 can be connected to, for example, an indwelling needle indwelled in a living body of a patient or the like. The female connector portion 101 is formed at a female connector side housing 103, the male connector portion 102 is formed at a male connector side housing 104, and the female connector side housing 103 and the male connector side housing 104 are coupled to each other.

The opening portion of the female connector portion 101 is provided with a valve body 105 which opens the opening portion to form a passage when the male connector portion 2 of the medical connector 1 is inserted thereinto and closes the opening portion when the male connector portion 2 is not inserted thereinto. In this example, an urging force is applied to an outer surface portion 105a of the valve body 105 toward an outer surface portion 101a of the female connector portion 101. A detailed structure for causing such an urging force is not illustrated in the drawings, but as such a structure, for example, a helical spring separated from the valve body 105 may be disposed inside the passage and a bellows-shaped elastic portion may be provided integrally with the outer surface portion 105a of the valve body 105.

In addition, a detailed structure in which the valve body 105 opens the opening portion of the female connector portion 101 to form a passage at the time of inserting the male connector portion 2 of the medical connector 1 is also not illustrated in the drawings. However, as such a structure, for example, the valve body 105 or the female connector side housing 103 may be appropriately provided with a groove which defines a part of the passage formed at the time of opening the opening portion of the female connector portion 101.

An outer peripheral surface of the cylindrical peripheral wall portion 101b of the female connector portion 101 is provided with a plurality of (in this example, two) engagement concave portions 106 corresponding to a plurality of (in this example, two) claws 3a of the engagement member E1.

Figure 4A:
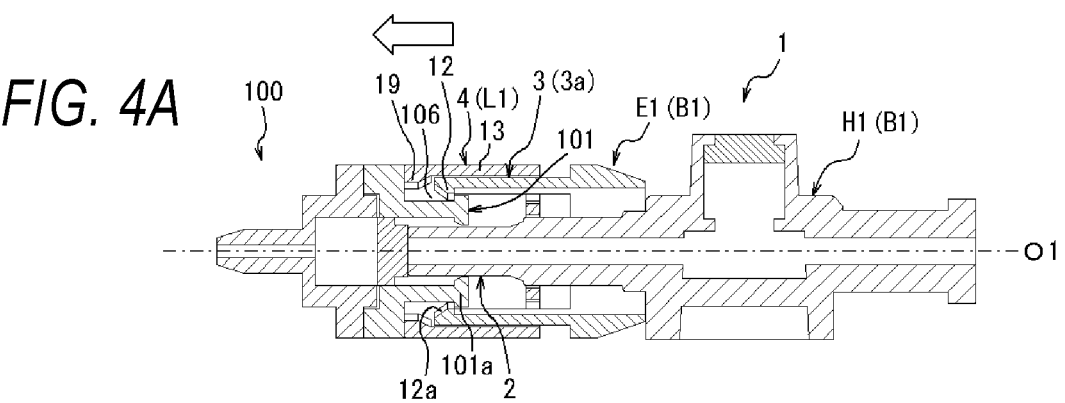
FIGS. 4A-4B illustrate a state at the time of starting the locking between the medical connector and the other medical connector illustrated in FIG. 1, where
Figure 4B:
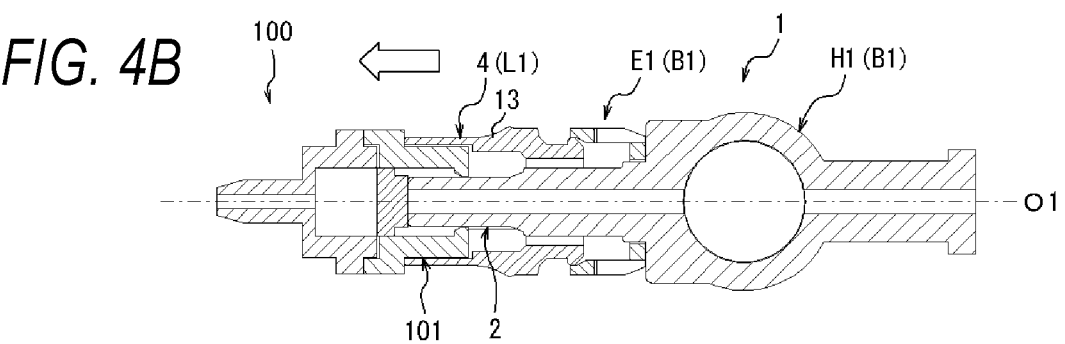

A method of connecting the medical connector 1 and the other medical connector 100 with the above-described configuration is as below. First, when the male connector portion 2 of the medical connector 1 is inserted into the female connector portion 101 of the other medical connector 100, for example, while the other medical connector 100 is held by a left hand and the connector body B1 of the medical connector 1 is held by a right hand from a state where the medical connector 1 and the other medical connector 100 are separated from each other as illustrated in FIGS. 1A-1C, the cylinder wall 13 of the locking member L1 comes into contact with the other medical connector 100 as illustrated in FIGS. 4A-4B.

At this time, since a gap between the engagement protrusions 12 of the plurality of claws 3a (a distance between the portions facing each other with the axis O1 interposed therebetween) is larger than an outer diameter of the outer surface portion 101a of the female connector portion 101, it is possible to allow the engagement protrusions 12 of the plurality of claws 3a of the engagement member E1 to climb over the outer surface portion 101a of the female connector portion 101 to face the engagement concave portion 106 without climbing over the outer surface portion 101a of the female connector portion 101 by the plurality of claws 3a. At that time, it is possible to smoothly guide the outer surface portion 101a of the female connector portion 101 between the plurality of claws 3a by the tapered surfaces 12a of the engagement protrusions 12 of the plurality of claws 3a.

Figure 5A:
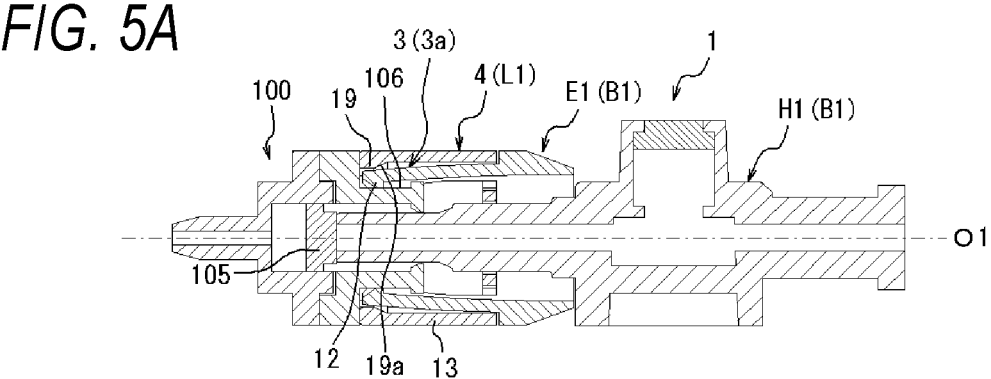
FIGS. 5A-5B illustrate a state at the time of completing the locking between the medical connector and the other medical connector illustrated in FIG. 1, where
Figure 5B:
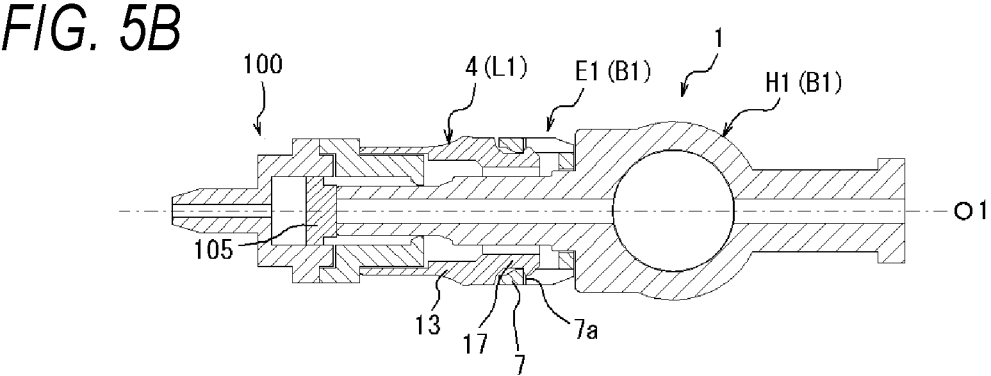

Then, when the male connector portion 2 is inserted more deeply, the cylinder wall 13 of the locking member L1 is pressed by the other medical connector 100 to slide on the engagement member E1 and the locking protrusion 19 formed at the cylinder wall 13 presses the plurality of claws 3a of the engagement member E1 to elastically deform the claws, a locked state where the plurality of claws 3a cannot be pulled out of the other medical connector 100 is set as illustrated in FIGS. 5A-5B. Here, in this example, the locked state indicates a state where the engagement protrusions 12 of the plurality of claws 3a are pressed by the locking protrusions 19 of the locking portion 4 (the locking member L1) to be positioned inside the engagement concave portions 106 of the female connector portion 101.

Further, since the plurality of claws 3a can be pressed through the tapered surfaces 19a of the locking protrusions 19 at the time of pressing the plurality of claws 3a of the engagement member E1 by the locking protrusions 19, it is possible to reduce an operation force for elastically deforming the plurality of claws 3a. In addition, the tapered surfaces 19a for reducing such an operation force may be provided at the plurality of claws 3a instead of the locking protrusions 19.

Further, when the cylinder wall 13 sets the plurality of claws 3a in the locked state, the fitting wall side fitting portion 7a and the cylinder wall side fitting portion 17 are fitted to each other, thereby preventing the cylinder wall 13 from sliding toward the other medical connector 1.

Figure 6A:
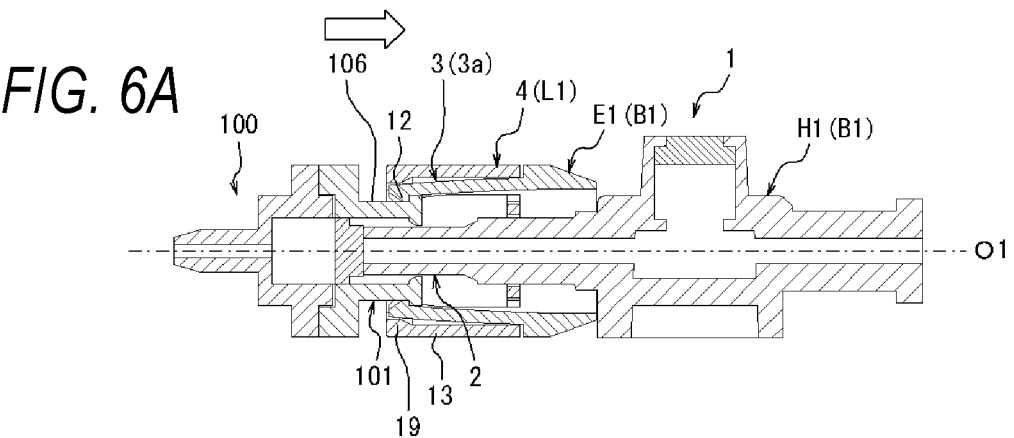
FIGS. 6A-6C illustrate a state at the time of completing the connection between the medical connector and the other medical connector illustrated in FIG. 1, where
Figure 6B:
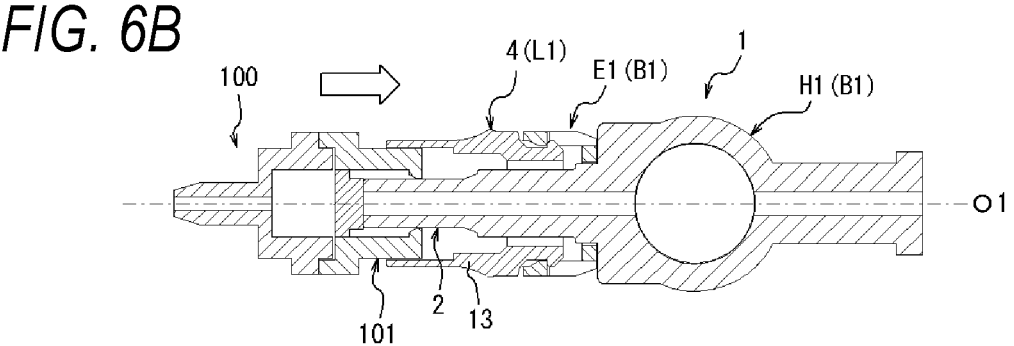
Figure 6C:
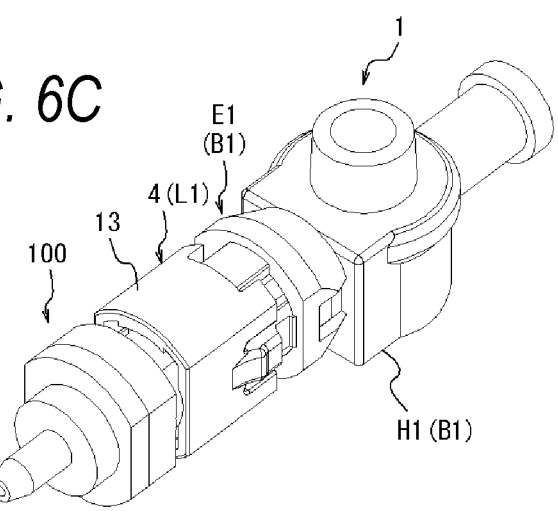

When the operation for the medical connector 1 and the other medical connector 100 ends in the above-described locked state, the medical connector 1 and the other medical connector 100 move in a direction in which both connectors are separated from each other by the urging force applied to the valve body 105 disposed inside the female connector portion 101, thereby setting a state where the engagement protrusions 12 of the plurality of claws 3a is locked by the end portion of the engagement concave portion 106, that is, the connectors are connected to each other as illustrated in FIGS. 6A-6C.

The medical connector 1 can be connected to the other medical connector 100 according to the above-described method, but there is no need to climb over the outer surface portion 101a of the female connector portion 101 by the plurality of claws 3a at the time of the connection. Thus, according to the medical connector 1, it is possible to suppress an unintended displacement of the other medical connector 100 at the time of the connection of the other medical connector 100. Further, in this embodiment, since the fitting protrusion 17a serving as the cylinder wall side fitting portion 17 is fitted to the opening portion serving as the fitting wall side fitting portion 7a when the plurality of claws 3a are in the locked state, it is needless to mention that the size and the shape of the fitting protrusion 17a are set to be sufficiently small to a degree that a force necessary for climbing over the fitting protrusion 17a at the time of the fitting does not cause an unintended displacement of the other medical connector 100.

Figure 7A:
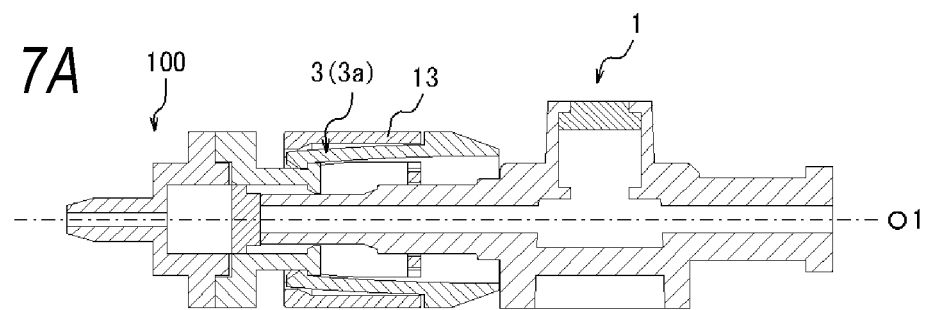
FIGS. 7A-7B illustrate a state at the time of starting the releasing of the locking between the medical connector and the other medical connector illustrated in FIG. 1, where
Figure 7B:
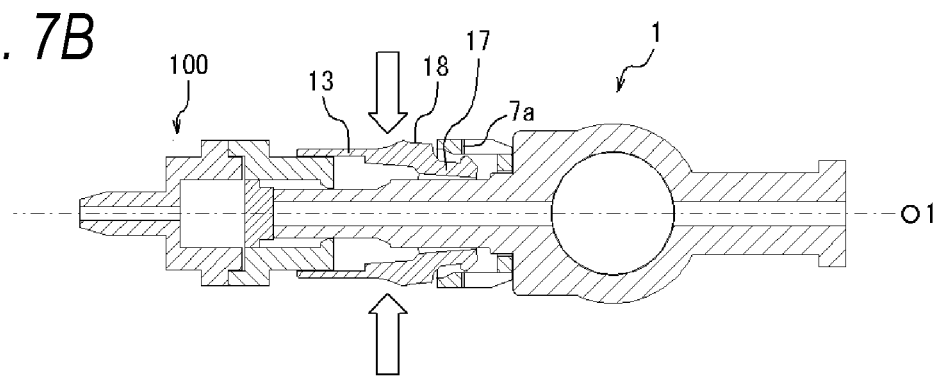

Next, a method of separating the medical connector 1 and the other medical connector 100 from each other will be described below. First, as illustrated in FIGS. 7A-7B, when the operation portion 18 provided at the cylinder wall 13 is pressed, the fitting between the fitting wall side fitting portion 7a and the cylinder wall side fitting portion 17 is released.

Figure 8A:
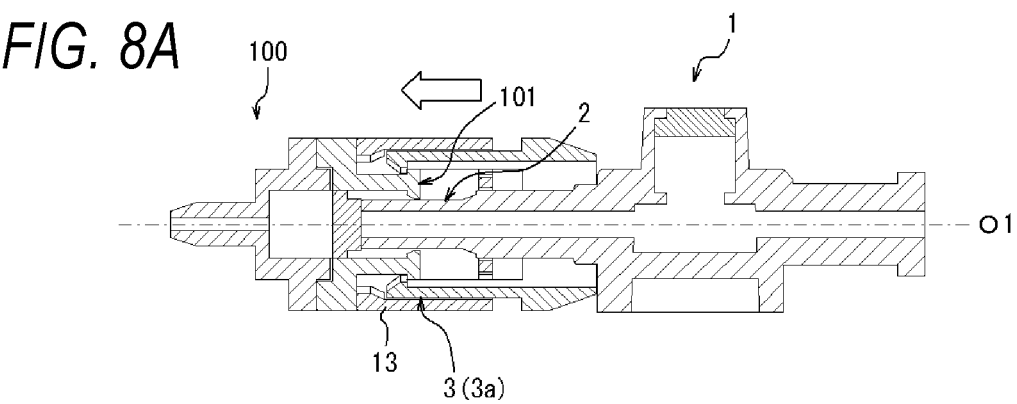
FIGS. 8A-8B illustrate a state at the time of completing the releasing of the locking between the medical connector and the other medical connector illustrated in FIG. 1, where
Figure 8B:
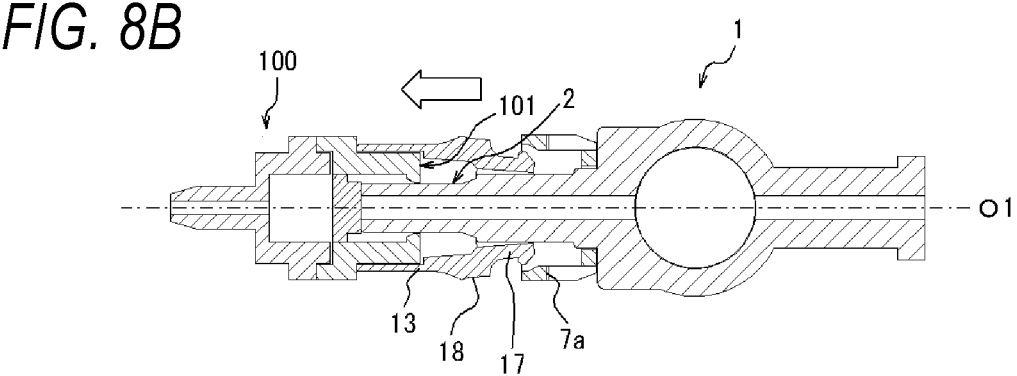
Figure 9A:
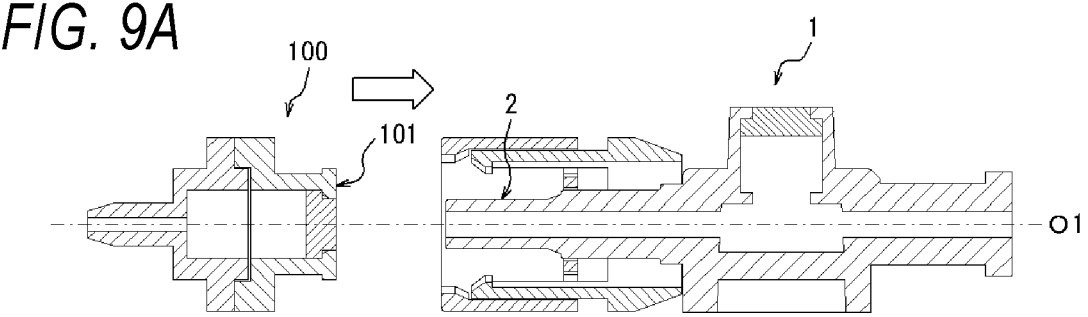
FIG. 9A-9B illustrate a state of completing the separation between the medical connector and the other medical connector illustrated in FIG. 1, where
Figure 9B:
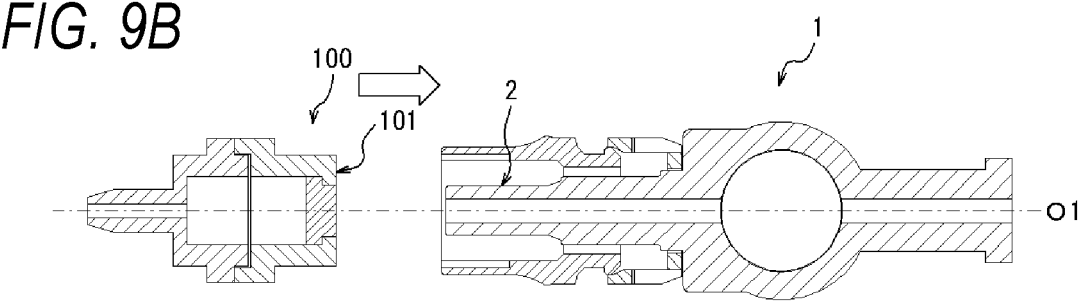

In this state, when the cylinder wall 13 is slid toward the other medical connector 100 as illustrated in FIGS. 8A-8B, the plurality of claws 3a are restored from the elastically deformed state so that the locking is released. Then, when the male connector portion 2 is removed from the female connector portion 101 as illustrated in FIG. 9A-9B, the connection between the connectors can be released.

As described above, according to the medical connector 1 of this embodiment, when the male connector portion 2 of the medical connector 1 is inserted into the female connector portion 101 of the other medical connector 100, the locking portion 4 (the locking member L1) slides on the engagement portion 3 (the plurality of claws 3a). Then, the locked state where the engagement portion 3 cannot be pulled out of the other medical connector 100 can be set by the locking portion 4 which slides in this way.

Thus, according to this embodiment, it is possible to connect the connectors to each other just by inserting the male connector portion 2 into the female connector portion 101 of the other medical connector 100. Further, according to this embodiment, since the engagement portion 3 can enter the locked state by the sliding of the locking portion 4, it is possible to connect the connectors to each other without climbing over a stepped portion of the other medical connector 100 by the engagement portion 3. Thus, according to this embodiment, it is possible to suppress an unintended displacement of the other medical connector 100 while ensuring the ease of the connection operation with respect to the other medical connector 100.

Further, in the medical connector 1 according to this embodiment, the engagement portion 3 includes the plurality of claws 3a and the locking portion 4 includes the cylinder wall 13 surrounding the plurality of claws 3a and the locking protrusion 19 formed at the inner peripheral surface of the cylinder wall 13. Thus, according to this embodiment, it is possible to obtain the above-described effect, that is, an effect capable of suppressing an unintended displacement of the other medical connector 100 while ensuring the ease of the connection operation with respect to the other medical connector 100 with a simple configuration.

Further, in the locking portion 4 of this embodiment, when the male connector portion 2 is inserted into the female connector portion 101 of the other medical connector 100, the cylinder wall 13 slides while being pressed by the other medical connector 100 and the locking protrusions 19 elastically deform the plurality of claws 3a in a pressed state, thereby setting the locked state where the plurality of claws 3a cannot be pulled out of the other medical connector 100. Thus, according to this embodiment, since it is possible to connect the connectors to each other just by inserting the male connector portion 2 of the medical connector 1 into the female connector portion 101 of the other medical connector 100 while gripping a portion other than the locking portion 4 of the medical connector 1 and the other medical connector 100, it is possible to obtain satisfactory operability.

Further, the medical connector 1 according to this embodiment includes the fitting wall 7 which is connected to the proximal end portions of the plurality of claws 3a and the fitting wall side fitting portion 7a and the cylinder wall side fitting portion 17 which are fitted to each other to prevent the cylinder wall 13 from sliding toward the other medical connector 100 when the cylinder wall 13 sets the plurality of claws 3a in the locked state are provided between the fitting wall 7 and the cylinder wall 13. Thus, according to this embodiment, it is possible to maintain the locked state with a simple configuration.

Further, in this embodiment, the cylinder wall 13 includes the operation portion 18 formed at the outer peripheral surface of the cylinder wall 13 and the fitting between the fitting wall side fitting portion 7a and the cylinder wall side fitting portion 17 is released by the pressing of the operation portion 18. Thus, according to this embodiment, since it is possible to release the locking by pressing the operation portion 18 provided at the cylinder wall 13 and sliding the cylinder wall 13 in this state, it is possible to obtain satisfactory operability.

Further, in this embodiment, it is necessary to perform two steps of operations of pressing the operation portion 18 and sliding the cylinder wall 13 in order to release the locking and it is necessary to slide the cylinder wall 13 which is a part of the medical connector 1 in a direction in which the cylinder wall moves close to the other medical connector 100 which is a separation target for that sliding. Thus, according to this embodiment, it is possible to reliably prevent an unintended separation of the connector.

In addition, in this embodiment, since two sets of the operation portion 18, the fitting wall side fitting portion 7a, and the cylinder wall side fitting portion 17 are provided at positions facing each other with the axis O1 interposed therebetween, it is possible to press two operation portions 18 just by grasping the operation portions 18 from the outer peripheral side with, for example, a thumb and a forefinger. Accordingly, it is possible to obtain more satisfactory operability.

Next, a medical connector 21 according to another embodiment will be described in detail with reference to FIGS. 10A to 14B.

In particular, the configuration of the medical connector 21 according to this embodiment is different from that of the above-described embodiment in that the locking portion 24 slides on the engagement portion 23 in a different direction.

As illustrated in FIGS. 10A to 12, the medical connector 21 according to this embodiment includes a male connector portion 22, an engagement portion 23, and a locking portion 24 and is connectable to the other medical connector 200. In this example, the male connector portion 22 is integrated with a housing H2. Further, in this example, the engagement portion 23 is formed at an engagement member E2 fixed to the housing H2 and is formed as a plurality of (in this example, two) claws 23a. In addition, in this example, the locking portion 24 is formed as a locking member L2 attached to the housing H2 to be slidable. The medical connector 21 according to this embodiment includes a connector body B2 including the housing H2 and the engagement member E2 and the locking member L2 attached to the connector body B2 to be slidable in the direction of an axis O2 of the male connector portion 22. The housing H2, the engagement member E2, and the locking member L2 can be formed of, for example, a synthetic resin.

The housing H2 is provided with a connection portion 25 which is formed at the opposite side of the male connector portion 22 to be connectable to an end portion of a tube connected to, for example, an infusion container. Instead of such a configuration, the housing H2 can be formed as a T-port connector or a three-way stopcock, for example, similarly to the above-described embodiment.

The engagement member E2 includes a bottom wall 40 which is connected to proximal end portions of the plurality of claws 23a. The bottom wall 40 includes a penetration hole 41 (see FIG. 12) into which the male connector portion 22 of the housing H2 is insertable and is fitted to an intermediate portion of the male connector portion 22 in the direction of the axis O2, so that the engagement member E2 is retained by the male connector portion 22. Further, the bottom wall 40 is provided with four protrusions 42 which extend toward the opposite side of the plurality of claws 23a. In addition, the number of the protrusions 42 provided at the bottom wall 40 can be appropriately increased or decreased. A distal end portion of each of the protrusions 42 is provided with an engagement member side convex portion 43 which generates a sense of clicking while climbing over a locking member side convex portion 46 which will be described later and is provided at the locking member L2. Further, the bottom wall 40 is provided with a pair of guide pieces 44 which extends in the same direction as those of the plurality of claws 23a. The pair of guide pieces 44 is configured to guide the sliding movement of a cylinder wall 33 to be described later in the locking member L2.

The locking member L2 includes the cylinder wall 33. A proximal end side end portion of the cylinder wall 33 is provided with a pair of protrusions 34 which protrudes toward the inner peripheral side. The pair of protrusions 34 is provided with four opening portions 45 into which four protrusions 42 provided in the engagement member E2 are insertable. In addition, the number of the opening portions 45 provided at the locking member L2 can be appropriately increased or decreased in accordance with the number of the protrusions 42 provided at the engagement member E2. Each opening portion 45 is provided with the locking member side convex portion 46 which generates a sense of clicking while climbing over the engagement member side convex portion 43.

The pair of protrusions 34 of the locking member L2 is disposed in a slidable manner between a flange 47 provided at the proximal end portion of the male connector portion 22 of the housing H2 and the bottom wall 40 of the engagement member E2 retained by the male connector portion 22. In addition, the distal end side of the flange 47 of the male connector portion 22 is provided with an annular convex portion 48 which generates a sense of clicking by the pair of protrusions 34 climbing over the annular convex portion when the pair of protrusions 34 of the locking member L2 moves to the proximal end side end portion in the movable range (until coming into contact with the flange 47). Further, the annular convex portion 48 also generates a sense of clicking by the pair of protrusions 34 climbing over the annular convex portion when the pair of protrusions 34 slides from the proximal end side end portion to the distal end portion of the movable range.

Further, a pair of convex portions 49 is formed at the inner peripheral side of the cylinder wall 33 of the locking member L2. The pair of convex portions 49 guides the locking member L2 while suppressing a sliding resistance between the locking member L2 and the engagement member E2 in such a manner that the convex portions slide on the guide pieces 44 of the engagement member E2 during the sliding movement of the locking member L2. In addition, the pair of convex portions 49 may not slide on the guide pieces 44. Further, the pair of convex portions 49 may not be provided.

Each of the plurality of claws 23a of the engagement member E2 is provided with a plate piece 31 which extends along the axis O2 and has a circular-arc cross-section, an engagement protrusion 32 which is formed at the distal end portion of the plate piece 31 to protrude toward the inner peripheral side, and an outer peripheral protrusion 50 which is formed at the distal end portion of the plate piece 31 to protrude toward the outer peripheral side. In addition, the outer peripheral protrusion 50 may protrude in relation to the proximal end side in the direction of the axis O2. For example, a configuration may be employed in which a groove extending along the axis O2 is provided at the outer peripheral surface of the plate piece 31 and the protrusion protrudes toward the distal end side of the groove. That is, the outer peripheral protrusion 50 does not need to have the highest circumferential height in the outer peripheral surface of the plate piece 3l. Each distal end surface of the engagement protrusions 32 of the plurality of claws 23a is formed as a tapered surface 32a of which a protruding width of the engagement protrusion 32 decreases toward the distal end side. Further, each proximal end surface of the outer peripheral protrusions 50 of the plurality of claws 23a is formed as a tapered surface 50a of which a protruding width of the outer peripheral protrusion 50 increases toward the distal end side.

Further, a tapered surface 39 which increases in diameter toward each of a plurality of (in this example, two) distal ends corresponding to the outer peripheral protrusions 50 of the plurality of claws 23a is provided in the vicinity of the distal end portion of the inner peripheral surface of the cylinder wall 33 of the locking member L2.

Figure 10A:
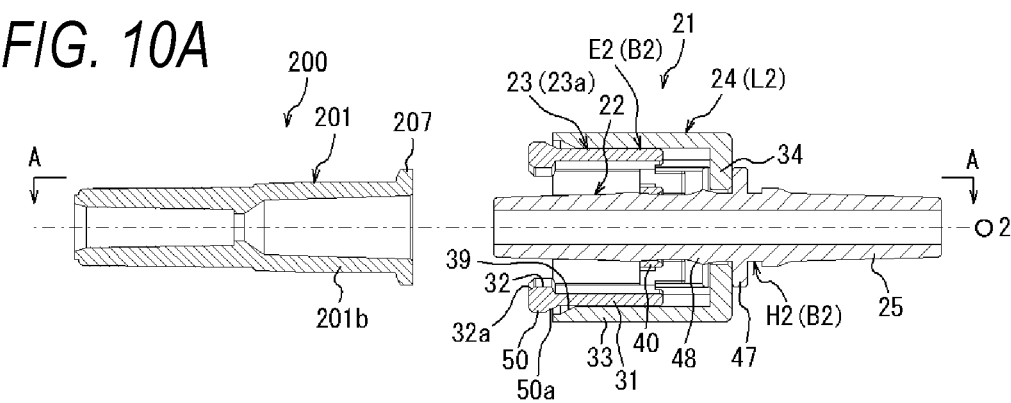
FIGS. 10A-10C illustrate a state of the separation between a medical connector according to another embodiment of the invention and the other medical connector, where
Figure 10B:
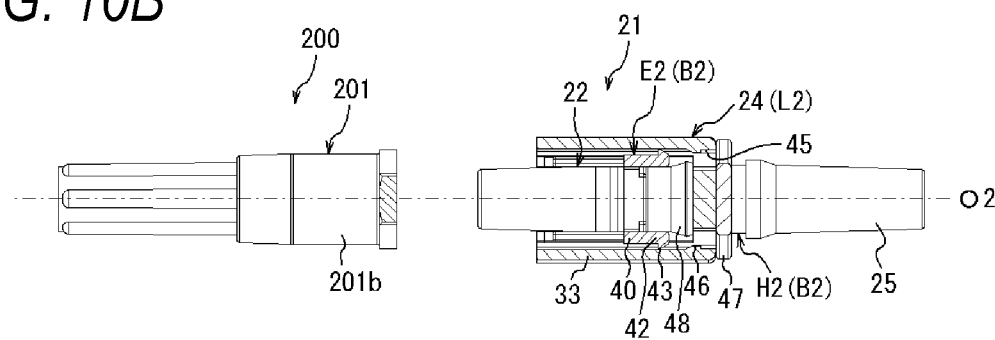
Figure 10C:
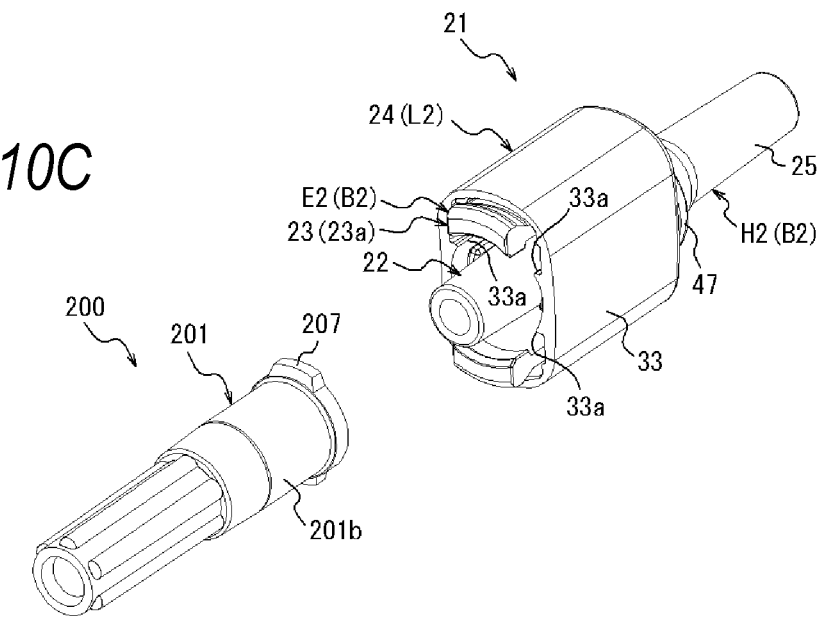
Figure 11:
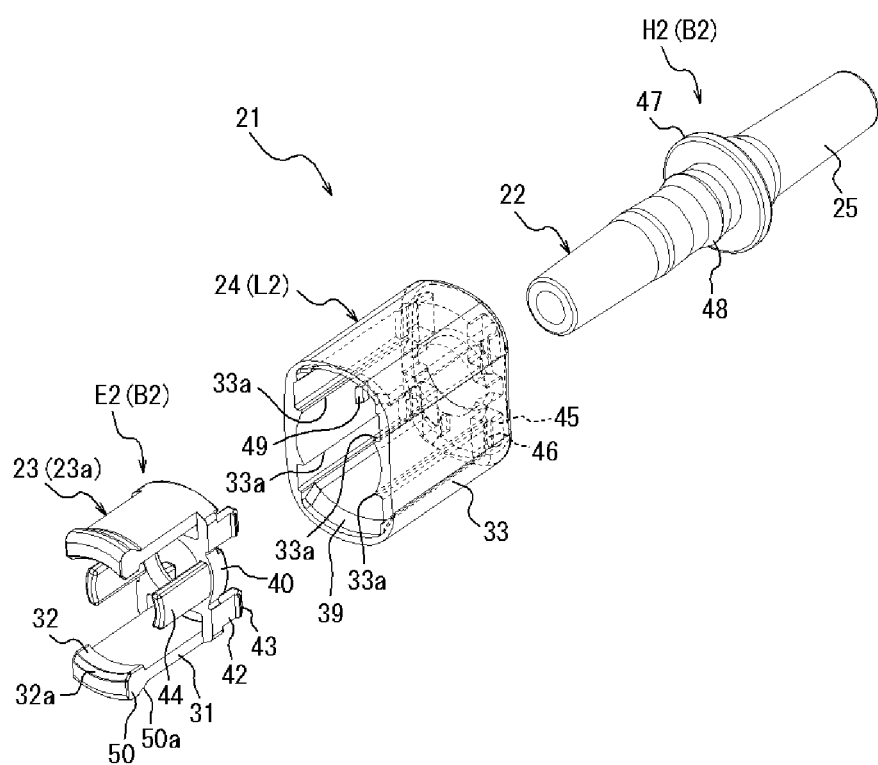
FIG. 11 is an exploded perspective view of the medical connector illustrated in FIG. 10.
Figure 12:
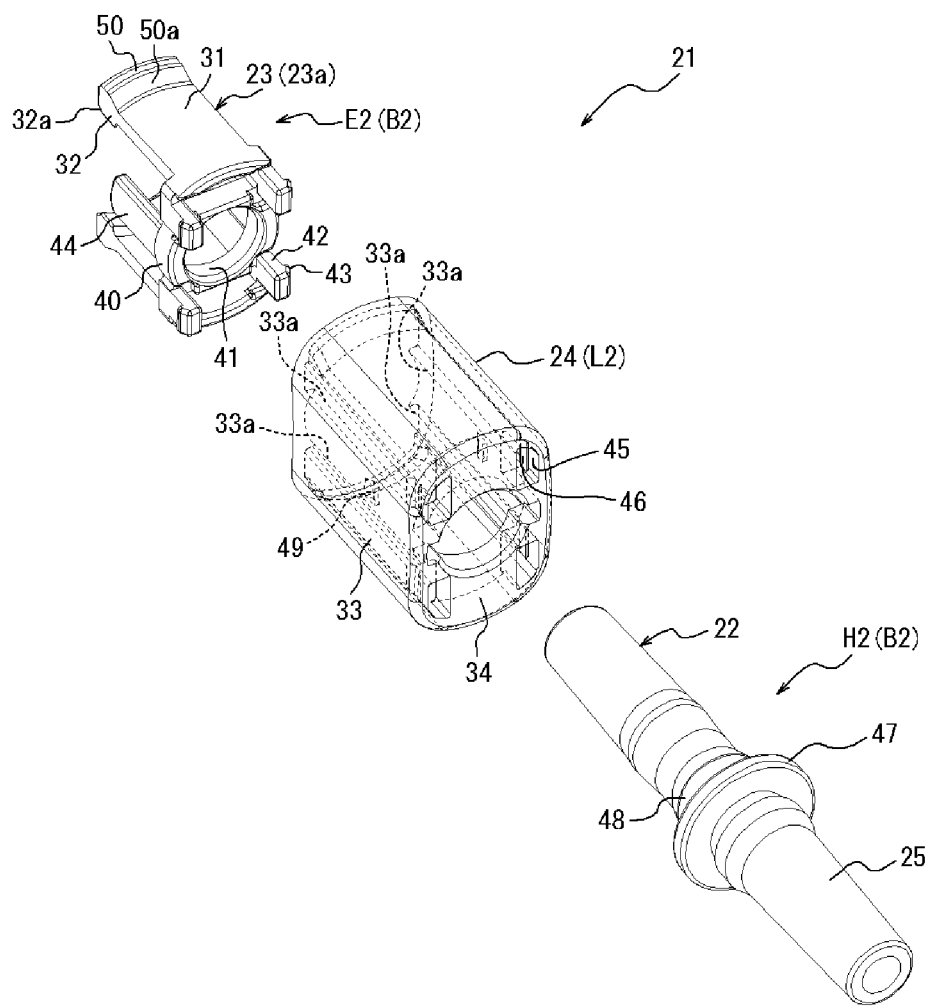
FIG. 12 is an exploded perspective view in which the medical connector illustrated in FIG. 10 is viewed from a different angle.

As illustrated in FIGS. 10A-10C, the other medical connector 200 includes a female connector portion 201. In this example, the other medical connector 200 is formed as an indwelling needle hub connected to an indwelling needle (not illustrated). An inner peripheral surface of the female connector portion 201 is formed in a tapered shape to decrease in diameter toward the distal end side and its inclination is set to be the same as the angle of the tapered outer peripheral surface of the male connector portion 22.

Further, a proximal end side end portion of a cylindrical peripheral wall portion 201b of the female connector portion 201 is provided with a plurality of (in this example, two) engagement convex portions 207 which protrude toward the outer peripheral side.

Figure 13A:
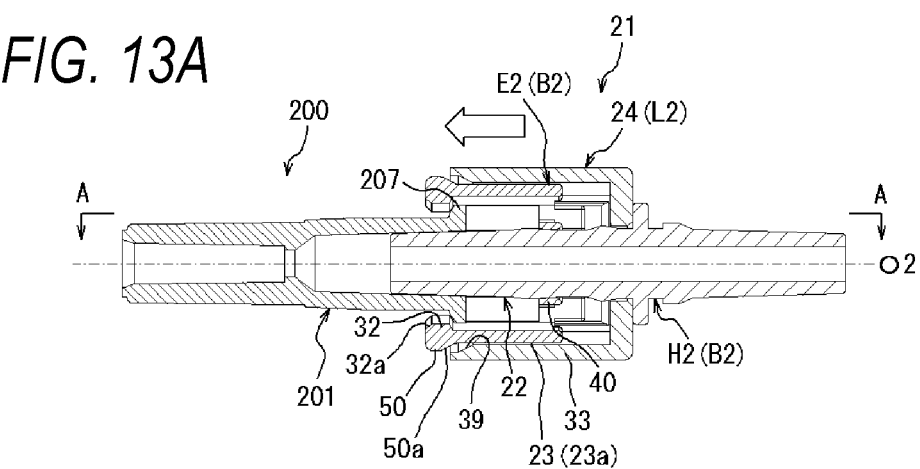
FIGS. 13A-13B illustrate a state at the time of starting the locking between the medical connector and the other medical connector illustrated in FIG. 10, where
Figure 13B:
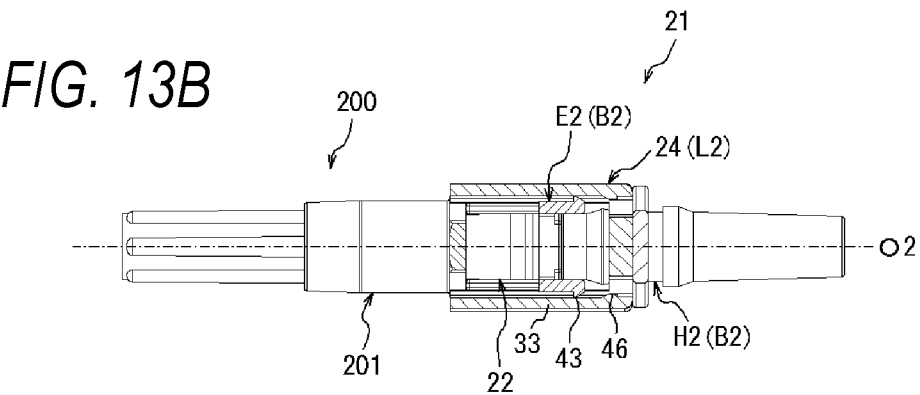

A method of connecting the medical connector 21 and the other medical connector 200 with the above-described configuration is as below. First, when the locking member L2 is moved in a direction moving close to the other medical connector 200 so that the male connector portion 22 of the medical connector 21 is inserted into the female connector portion 201 of the other medical connector 200, for example, while the other medical connector 200 is held by a left hand and the locking member L2 of the medical connector 21 is held by a right hand from a state where the medical connector 21 and the other medical connector 200 are separated from each other as illustrated in FIGS. 10A-10C, the outer peripheral surface of the distal end portion of the male connector portion 22 comes into contact with the inner peripheral surface of the proximal end portion of the female connector portion 201 as illustrated in FIGS. 13A-13B.

At this time, since a gap between the engagement protrusions 32 of the plurality of claws 23a (in this example, a distance between the portions facing each other with the axis O2 interposed therebetween) is larger than an outer diameter of a portion provided with the engagement convex portion 207 of the female connector portion 201 (in this example, a distance between the portions facing each other with the axis O2 interposed therebetween at the outer peripheral end portions of two engagement convex portions 207), the engagement protrusions 32 of the plurality of claws 23a of the engagement member E2 can climb over the engagement convex portions 207 of the female connector portion 201 without climbing over the engagement convex portion 207 of the female connector portion 201 by the plurality of claws 23a. At that time, it is possible to smoothly guide the engagement convex portion 207 of the female connector portion 201 between the plurality of claws 23a by the tapered surfaces 32a of the engagement protrusions 32 of the plurality of claws 23a.

Figure 14A:
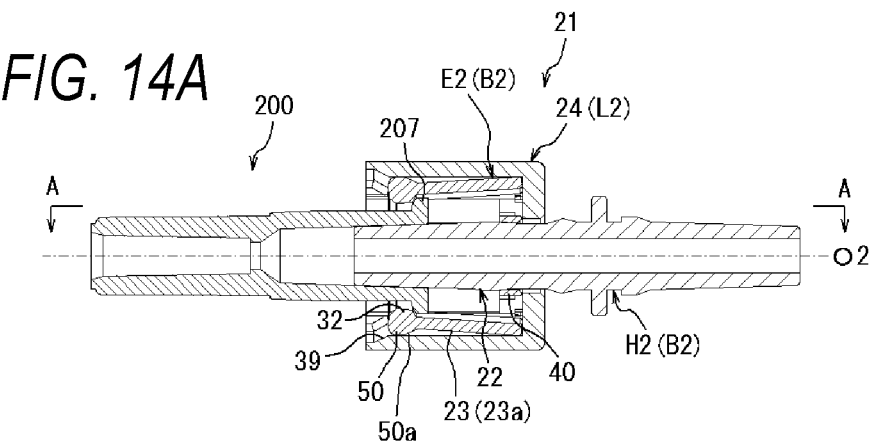
FIGS. 14A-14B illustrate a state at the time of completing the locking between the medical connector and the other medical connector illustrated in FIG. 10, where
Figure 14B:
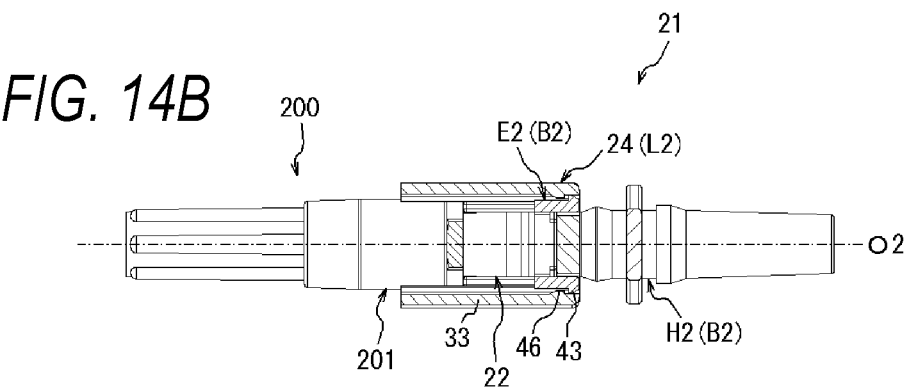

Then, when the locking member L2 is further moved in a direction of moving close to the other medical connector 200, the connector body B2 (the housing H2 and the engagement member E2) cannot move anymore and thus the locking member L2 slides on the engagement member E2. For this reason, when the cylinder wall 33 presses the outer peripheral protrusions 50 of the plurality of claws 23a of the engagement member E2 to elastically deform the plurality of claws 23a, a locked state where the plurality of claws 23a cannot be pulled out of the other medical connector 200 is set as illustrated in FIGS. 14A-14B. Here, in this example, the locked state indicates a state where the engagement protrusions 32 of the plurality of claws 23a are pressed by the cylinder wall 33 of the locking portion 24 (the locking member L2) to be retained by the engagement convex portions 207 of the female connector portion 201. Further, in this example, a connection between the connectors is completed at a time point of the locked state.

In addition, in this example, in order to reliably maintain the locked state and the connection state, a relative rotation about the axis O2 between the female connector portion 201 and the locking member L2 is prohibited. Specifically, the cylinder wall 33 of the locking member L2 includes a rotation regulation portion 33a (see FIG. 10C) which prohibits the rotation of the female connector portion 201 relative to the cylinder wall 33 in such a connection state. In this example, the rotation regulation portion 33a is formed as a convex portion which protrudes from the inner peripheral surface of the cylinder wall 33. Here, when the female connector portion 201 rotates relative to the cylinder wall 33, the further rotation of the female connector portion 201 is prohibited due to the contact with the engagement convex portions 207 of the female connector portion 201. Accordingly, it is possible to maintain the locked state between the plurality of engagement convex portions 207 and the engagement protrusions 32 of the plurality of claws 23a.

Further, since the plurality of claws 23a can be pressed through the tapered surface 39 provided at the inner peripheral surface of the cylinder wall 33 and the tapered surface 50a of the outer peripheral protrusion 50 at the time of pressing the outer peripheral protrusions 50 of the plurality of claws 23a of the engagement member E2 by the cylinder wall 33 for the above-described locked state, it is possible to reduce an operation force for elastically deforming the plurality of claws 23a. In addition, any one of the tapered surface 39 and the tapered surface 50a for reducing the operation force may be omitted.

Further, when the cylinder wall 33 sets the plurality of claws 23a in the locked state, four locking member side convex portions 46 climb over four engagement member side convex portions 43 to generate a sense of clicking. Thus, the operator can easily check whether the locking is completed by the sense of clicking.

The medical connector 21 can be connected to the other medical connector 200 according to the above-described method, but there is no need to climb over the engagement convex portion 207 of the female connector portion 201 by the plurality of claws 23a at the time of the connection. Thus, according to the medical connector 21, it is possible to suppress an unintended displacement of the other medical connector 200 at the time of connecting the medical connector to the other medical connector 200. Additionally, in this embodiment, the protrusions (the annular convex portion 48, the locking member side convex portion 46, and the engagement member side convex portion 43) generating a sense of clicking are provided. However, it is needless to mention that the size and the shape of the protrusion are set to be sufficiently small to a degree that a force necessary for climbing over the protrusion at the time of generating a sense of clicking does not cause an unintended displacement of the other medical connector 200.

After the connectors are connected to each other, for example, the connectors are attached to a skin of a living body of a patient having an indwelling needle indwelled therein so that the female connector portion 201 and the locking member L2 are covered by an adhesive sheet such as a dressing film. Accordingly, since the movement of the locking member L2 is prevented, it is possible to reliably prevent an unintended separation of the connector. Further, an unintended separation of the connectors may be reliably prevented by prohibiting the releasing of the locking at the time of first completing the locking using the locking member L2 in such a manner that the protruding widths of the locking member side convex portion 46 and the engagement member side convex portion 43 are enlarged.

As described above, according to the medical connector 21 of this embodiment, when the male connector portion 22 of the medical connector 21 is inserted into the female connector portion 201 of the other medical connector 200, the locking portion 24 (the locking member L2) slides on the engagement portion 23 (the plurality of claws 23a) and a locked state where the engagement portion 23 cannot be pulled out of the other medical connector 200 can be set by the locking portion 24 sliding in this way.

Thus, according to this embodiment, it is possible to connect the connectors to each other just by inserting the male connector portion 22 into the female connector portion 201 of the other medical connector 200. Further, according to this embodiment, since the engagement portion 23 can be set to the locked state by the sliding of the locking portion 24, it is possible to connect the connectors to each other without climbing over the stepped portion of the other medical connector 200 by the engagement portion 23. Thus, according to this embodiment, it is possible to suppress an unintended displacement of the other medical connector 200 while ensuring the ease of a connection operation with respect to the other medical connector 200.

Further, in the medical connector 21 according to this embodiment, the engagement portion 23 includes the plurality of claws 23a and the outer peripheral protrusion 50 formed at the outer peripheral surfaces of the plurality of claws 23a and the locking portion 24 includes the cylinder wall 33 surrounding the plurality of claws 23a. Thus, according to this embodiment, it is possible to obtain the above-described effect, that is, an effect capable of suppressing an unintended displacement of the other medical connector 200 while ensuring the ease of a connection operation with respect to the other medical connector 200 with a simple configuration.

Further, in the locking portion 24 of this embodiment, when the male connector portion 22 is inserted into the female connector portion 201 of the other medical connector 200, the male connector portion 22 slides while coming into contact with the female connector portion 201 and the cylinder wall 33 presses the outer peripheral protrusion 50 to elastically deform the plurality of claws 23a, so that a locked state where the plurality of claws 23a cannot be pulled out of the other medical connector 200 is set. Thus, according to this embodiment, since it is possible to connect the connectors to each other just by inserting the male connector portion 22 of the medical connector 21 into the female connector portion 201 of the other medical connector 200 while gripping the other medical connector 200 and the locking portion 24 of the medical connector 21, it is possible to obtain satisfactory operability.

Further, in this embodiment, the cylinder wall 33 of the locking portion 24 includes the rotation regulation portion 33a which prohibits the rotation of the female connector portion 201 of the other medical connector 200 relative to the cylinder wall 33. Thus, according to this embodiment, it is possible to reliably maintain the locked state and the connection state.

Next, a modified example of the medical connector 21 described with reference to FIGS. 10A to 14B will be described in detail with reference to FIGS. 15A to 19B.

In a medical connector 21A of this modified example, similarly to the medical connector 21 described with reference to FIGS. 10A to 14B, when a male connector portion 22A is inserted into the female connector portion 201 of the other medical connector 200, the male connector portion 22A comes into contact with the female connector portion 201 to cause the sliding of a locking portion 24A and a cylinder wall 33A presses an outer peripheral protrusion 50A to elastically deform a plurality of claws 23aA. Accordingly, a locked state where the plurality of claws 23aA cannot be pulled out of the other medical connector 200 can be set.

However, the medical connector 21A of this modified example is different from the medical connector 21 described with reference to FIGS. 10A to 14B in that the male connector portion 22A includes a sealing portion 22aA sealing an outer surface 201a of the female connector portion 201. In addition, the other medical connector 200 connected to the medical connector 21A of this modified example has the same configuration as that of FIGS. 10A-10C.

As illustrated in FIGS. 15A to 17, the medical connector 21A of this modified example includes the male connector portion 22A, an engagement portion 23A, and the locking portion 24A and is connectable to the other medical connector 200. In this example, the male connector portion 22A is integrated with a housing H2A. Further, in this example, the engagement portion 23A is formed at an engagement member E2A fixed to the housing H2A and is formed as a plurality of (in this example, two) claws 23aA. Additionally, in this example, the locking portion 24A is formed as a locking member L2A attached to the housing H2A to be slidable.

Further, in this modified example, the male connector portion 22A includes the sealing portion 22aA as described above. In this example, the sealing portion 22aA is formed as an annular sealing member S2A which is fixed by fitting to an annular concave portion 22bA circumferentially provided at the outer peripheral surface of the male connector portion 22A of the housing H2A. The sealing portion 22aA includes a conical tapered surface 22a1A which increases in diameter toward the proximal end side at the time of the connection to the male connector portion 22A and a disc-shaped sealing flange 22a2A which increases in diameter from the proximal end side edge of the tapered surface 22a1A.

The medical connector 21A of this modified example includes the housing H2A, a connector body B2A including the engagement member E2A and the sealing member S2A, and the locking member L2A attached to the connector body B2A to be slidable in the direction along the axis O2 of the male connector portion 22A. The housing H2A, the engagement member E2A, and the locking member L2A can be formed of, for example, a synthetic resin. Further, the sealing member S2A can be formed of, for example, an elastic material such as rubber or thermoplastic elastomer.

The housing H2A is provided with a connection portion 25A which is formed at the opposite side of the male connector portion 22A to be connectable to an end portion of a tube connected to, for example, an infusion container. Instead of such a configuration, the housing H2A can be formed as a T-port connector or a three-way stopcock, for example, similarly to the above-described embodiment.

The engagement member E2A includes a bottom wall 40A which is connected to the proximal end portions of the plurality of claws 23aA. The bottom wall 40A includes a penetration hole 41A (see FIG. 17) into which the male connector portion 22A of the housing H2A is insertable and is fitted to an intermediate portion of the male connector portion 22A in the direction of the axis O2, so that the engagement member E2A is retained by the male connector portion 22A. Further, the bottom wall 40A is provided with four protrusions 42A which extend toward the opposite side of the plurality of claws 23aA. In addition, the number of the protrusions 42A provided at the bottom wall 40A can be appropriately increases or decreased. A distal end portion of each protrusion 42A is provided with an engagement member side convex portion 43A which generates a sense of clicking when a locking member side convex portion 46A which is provided at the locking member L2A and will be described later climbs over the convex portion. Further, the bottom wall 40A is provided with a cylindrical guide piece 44A which extends in the same direction as those of the plurality of claws 23aA. The guide piece 44A guides the sliding movement of the cylinder wall 33A of the locking member L2A.

The locking member L2A includes the cylinder wall 33A. A proximal end side end portion of the cylinder wall 33A is provided with a pair of protrusions 34A which protrudes toward the inner peripheral side. The pair of protrusions 34A is provided with four opening portions 45A into which four protrusions 42A provided at the engagement member E2A are insertable. In addition, the number of the opening portions 45A provided at the locking member L2A can be appropriately increased or decreased in accordance with the number of the protrusions 42A provided at the engagement member E2A. Each opening portion 45A is provided with a locking member side convex portion 46A which generates a sense of clicking when the engagement member side convex portion 43A climbs over the convex portion.

The pair of protrusions 34A of the locking member L2A is disposed in a slidable manner between a flange 47A provided at the proximal end portion of the male connector portion 22A of the housing H2A and the bottom wall 40A of the engagement member E2A retained by the male connector portion 22A. In addition, each of the pair of protrusions 34A includes two protrusions 34aA and the totally four protrusions 34aA are disposed inside totally four groove portions 22cA formed at the distal end side of the flange 47A of the male connector portion 22A, so that the locking member L1A is attached to the male connector portion 22A of the housing H1A to be slidable.

Further, a pair of convex portions 49A is formed at the inner peripheral side of the cylinder wall 33A of the locking member L2A. The pair of convex portions 49A guides the locking member L2A while suppressing a sliding resistance between the locking member L2A and the engagement member E2A in such a manner that the convex portions slide on the guide piece 44A of the engagement member E2A during the sliding movement of the locking member L2A. In addition, the pair of convex portions 49A may not slide on the guide piece 44A. Further, the pair of convex portions 49A may not be provided.

Each of the plurality of claws 23aA of the engagement member E2A includes a plate piece 31A which has a circular-arc cross-section and extends along the axis O2, an engagement protrusion 32A which protrudes toward the inner peripheral side of the distal end portion of the plate piece 31A, and the outer peripheral protrusion 50A which is provided at the distal end portion of the plate piece 31 to protrude toward the outer peripheral side. Each distal end surface of the engagement protrusions 32A of the plurality of claws 23aA is formed as a tapered surface 32aA of which a protruding width of the engagement protrusion 32A decreases toward the distal end side. Further, each proximal end surface of the outer peripheral protrusions 50A of the plurality of claws 23aA is formed as a tapered surface 50aA of which a protruding width of the outer peripheral protrusion 50A increases toward the distal end side.

In addition, it is desirable to provide the sealing portion 22aA so that at least a part is disposed at the proximal end side in relation to the engagement protrusion 32A in the direction of the axis O2. With such an arrangement, it is possible to easily ensure the air-tightness at the proximal end side edge of the inner peripheral surface 201c of the female connector portion 201 and the inner peripheral edge of the outer surface 201a.

Further, a tapered surface 39A which increases in diameter toward a plurality of (in this example, two) distal ends corresponding to the outer peripheral protrusions 50A of the plurality of claws 23aA is provided in the vicinity of the distal end portion of the inner peripheral surface of the cylinder wall 33A of the locking member L2A.

Figure 15A:
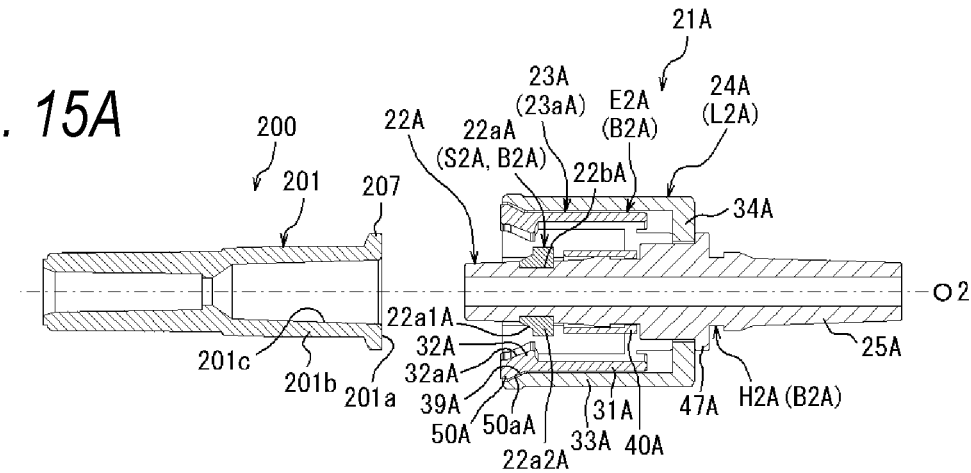
FIGS. 15A-15C illustrate a state at the time of the separation between a modified example of the medical connector illustrated in FIG. 10 and the other medical connector, where
Figure 15B:
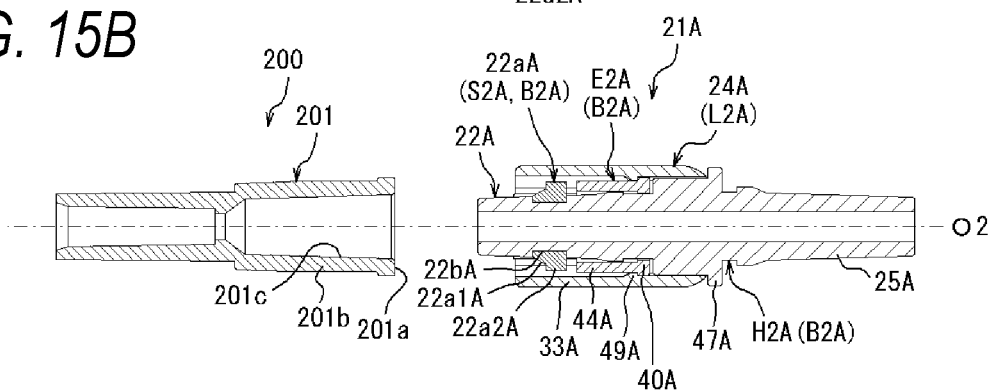
Figure 15C:
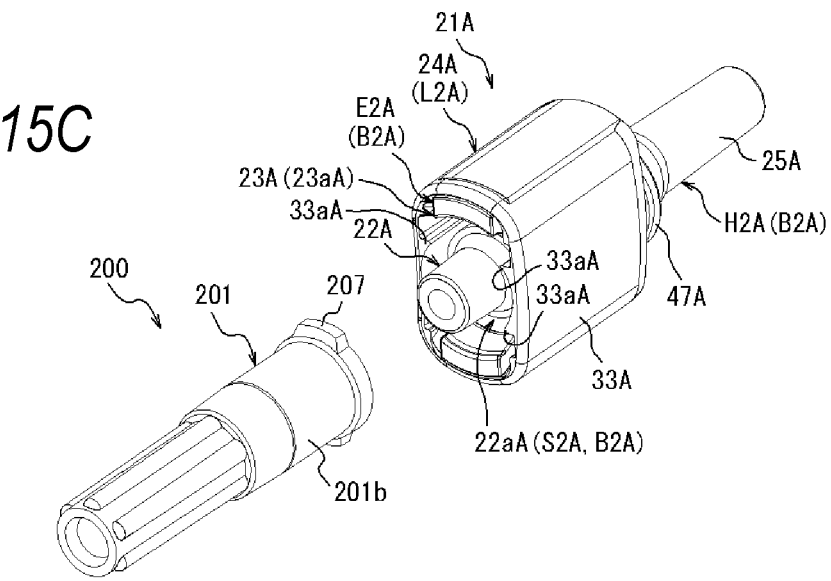
Figure 16:
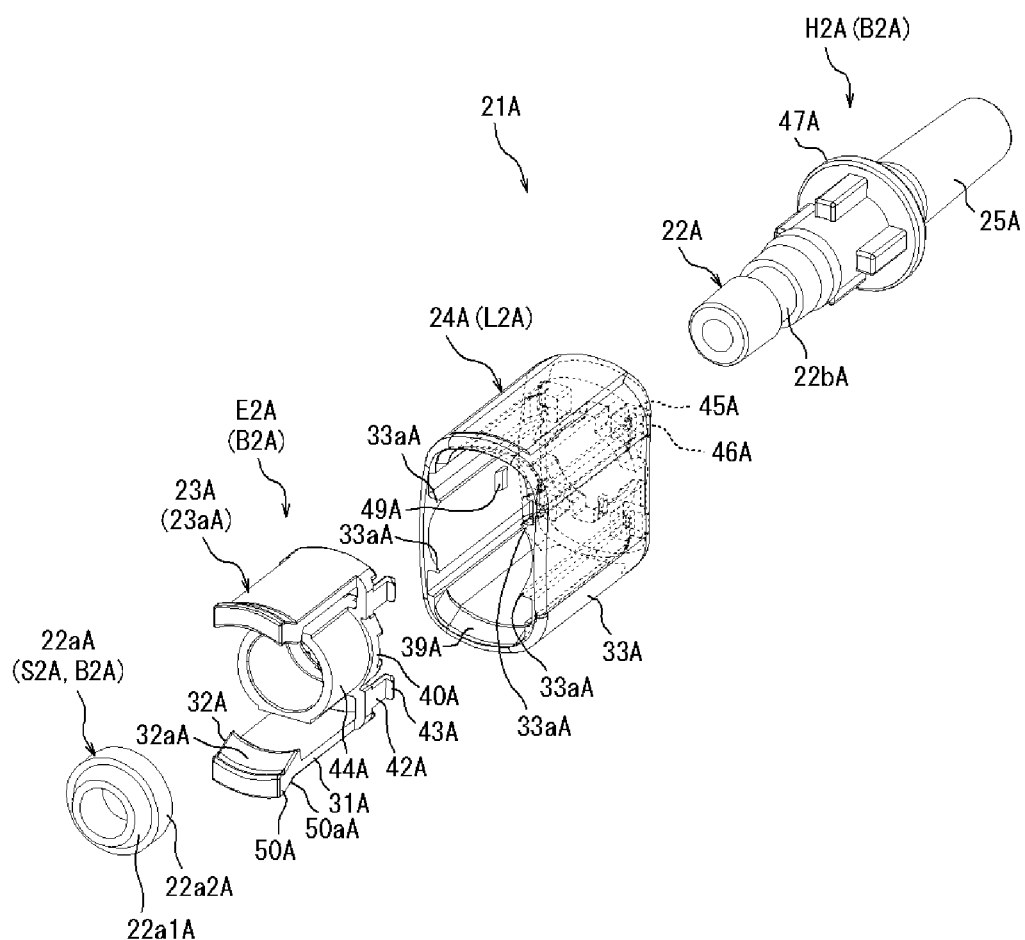
FIG. 16 is an exploded perspective view of the medical connector illustrated in FIG. 15.
Figure 17:
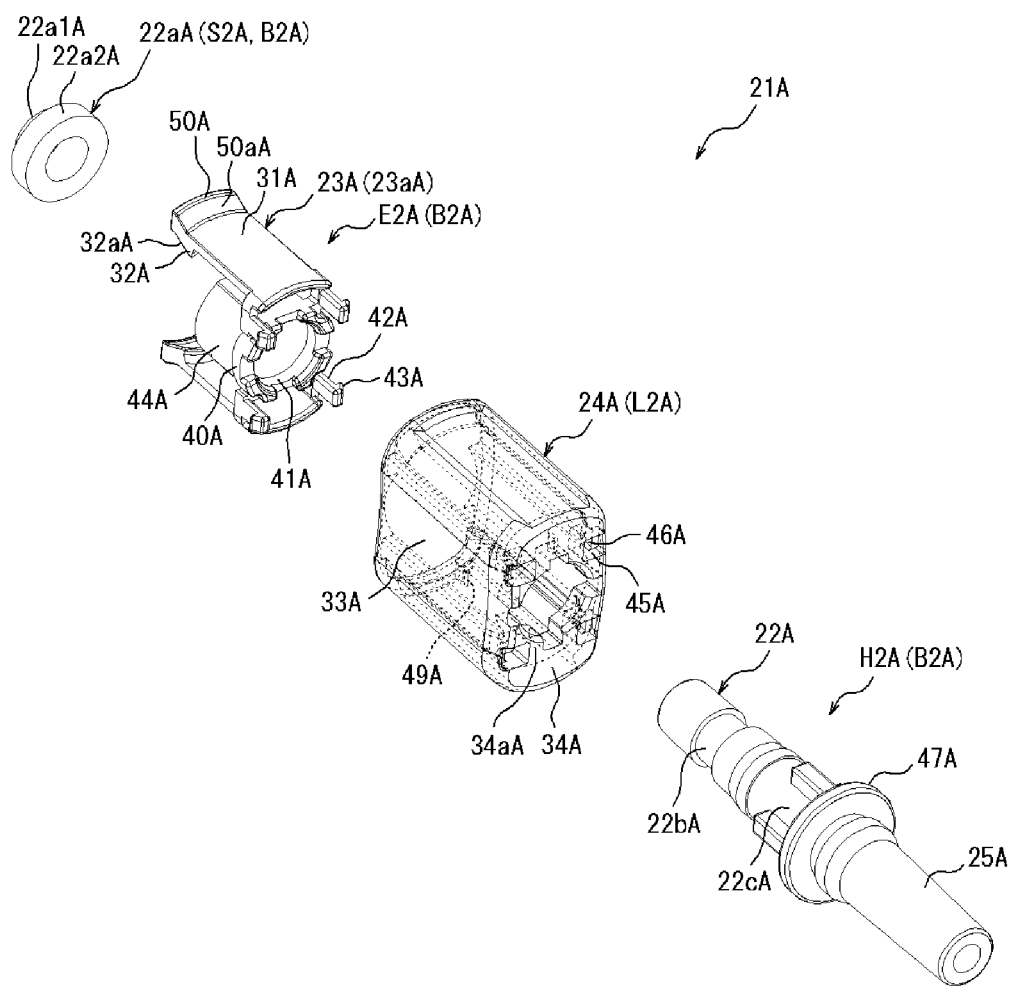
FIG. 17 is an exploded perspective view in which the medical connector illustrated in FIG. 15 is viewed from a different angle.
Figure 18A:
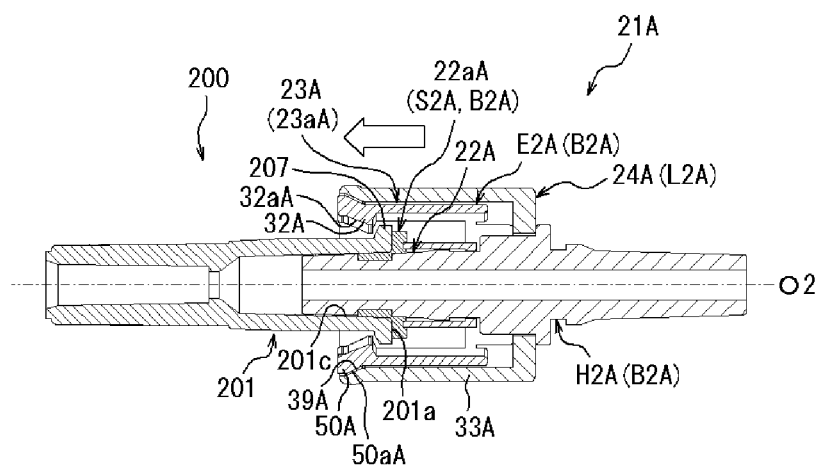
FIGS. 18A-18B illustrate a state at the time of starting the locking between the medical connector and the other medical connector illustrated in FIG. 15, where
Figure 18B:
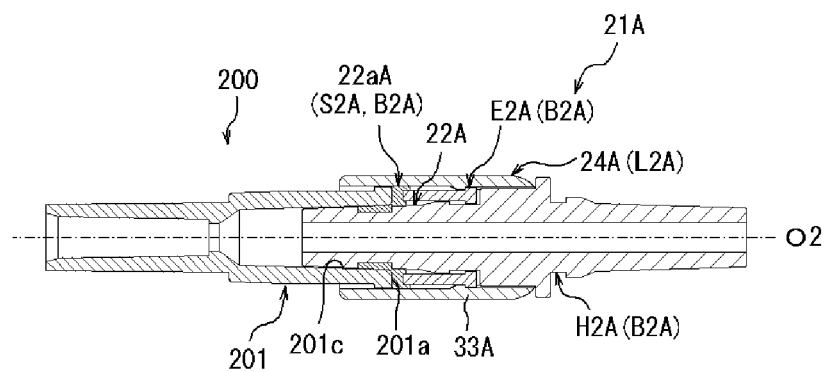

A method of connecting the medical connector 21A and the other medical connector 200 with the above-described configuration is as below. First, when the locking member L2A is moved in a direction moving close to the other medical connector 200 so that the male connector portion 22A of the medical connector 21A is inserted into the female connector portion 201 of the other medical connector 200, for example, while the other medical connector 200 is held by a left hand and the locking member L2A of the medical connector 21A is held by a right hand from a state where the medical connector 21A and the other medical connector 200 are separated from each other as illustrated in FIGS. 15A-15C, the outer surface 201a of the female connector portion 201 comes into contact with the sealing portion 22aA of the male connector portion 22A so that the outer surface 201a of the female connector portion 201 is sealed as illustrated in FIGS. 18A-18B.

At this time, since the sealing portion 22aA includes the tapered surface 22a1A (see FIGS. 15A-15C) which increases in diameter toward the proximal end side, it is possible to easily ensure the liquid-tightness at the proximal end side edge of the inner peripheral surface 201c of the female connector portion 201 and the inner peripheral edge of the outer surface 201a.

Further, at this time, since a gap between the engagement protrusions 32A of the plurality of claws 23aA (in this example, a distance between the portions facing each other with the axis O2 interposed therebetween) is larger than an outer diameter of a portion provided with the engagement convex portion 207 of the female connector portion 201 (in this example, a distance between the portions facing each other with the axis O2 interposed therebetween at the outer peripheral end portions of two engagement convex portion 207), the engagement convex portion 207 of the female connector portion 201 can climb over the engagement protrusions 32A of the plurality of claws 23aA of the engagement member E2A without climbing over the engagement convex portion 207 of the female connector portion 201 by the plurality of claws 23aA. At that time, it is possible to smoothly guide the engagement convex portion 207 of the female connector portion 201 between the plurality of claws 23aA by the tapered surfaces 32aA of the engagement protrusions 32A of the plurality of claws 23aA.

Figure 19A:
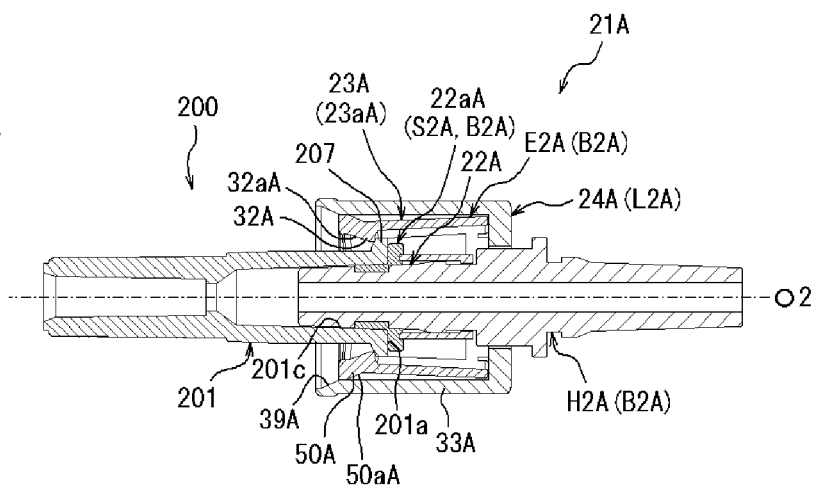
FIGS. 19A-19B illustrate a state at the time of completing the locking between the medical connector and the other medical connector illustrated in FIG. 15, where
Figure 19B:
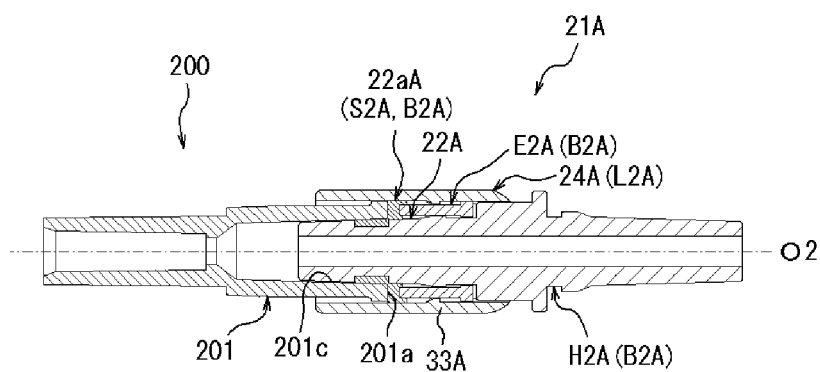

Then, when the locking member L2A is further moved in a direction of moving close to the other medical connector 200, the connector body B2A (the housing H2A, the engagement member E2A, and the sealing member S2A) cannot move anymore and thus the locking member L2A slides on the engagement member E2A. For this reason, since the cylinder wall 33A presses the outer peripheral protrusions 50A of the plurality of claws 23aA of the engagement member E2A to elastically deform the plurality of claws 23aA, a locked state where the plurality of claws 23aA cannot be pulled out of the other medical connector 200 can be set as illustrated in FIGS. 19A-19B. Here, in this example, the locked state indicates a state where the engagement protrusions 32A of the plurality of claws 23aA are pressed by the cylinder wall 33A of the locking portion 24A (the locking member L2A) to be retained by the engagement convex portion 207 of the female connector portion 201. Further, in this example, a connection between the connectors is completed at a time point of the locked state.

In addition, in this example, a relative rotation about the axis O2 between the female connector portion 201 and the locking member L2A is regulated in order to reliably maintain the locked state and the connection state. Specifically, the cylinder wall 33A of the locking member L2A includes a rotation regulation portion 33aA (see FIG. 15C) which prohibits the rotation of the female connector portion 201A relative to the cylinder wall 33A in such a connection state. In this example, the rotation regulation portion 33aA is formed as a convex portion protruding from the inner peripheral surface of the cylinder wall 33A. Here, when the female connector portion 201 rotates relative to the cylinder wall 33A, the further rotation of the female connector portion 201 is prohibited due to the contact with the engagement convex portions 207 of the female connector portion 201. Accordingly, it is possible to maintain the locked state between the plurality of engagement convex portions 207 and the engagement protrusions 32A of the plurality of claws 23aA.

Further, since the plurality of claws 23aA can be pressed through the tapered surface 39A provided at the inner peripheral surface of the cylinder wall 33A and the tapered surface 50aA provided at the outer peripheral protrusion 50A at the time of pressing the outer peripheral protrusions 50A of the plurality of claws 23aA of the engagement member E2A by the cylinder wall 33A for the above-described locked state, it is possible to reduce an operation force for elastically deforming the plurality of claws 23aA. In addition, any one of the tapered surface 39A and the tapered surface 50aA for reducing such an operation force may be omitted.

Further, when the cylinder wall 33A sets the plurality of claws 23aA in the locked state, four locking member side convex portions 46A (see FIG. 17) climb over four engagement member side convex portions 43A so that a sense of clicking is generated. Thus, the operator can easily check whether the locking is completed by the sense of clicking.

The medical connector 21A can be connected to the other medical connector 200 according to the above-described method, but there is no need to climb over the engagement convex portion 207 of the female connector portion 201 by the plurality of claws 23aA at the time of the connection. Thus, according to the medical connector 21A, it is possible to suppress an unintended displacement of the other medical connector 200 at the time of the connection to the other medical connector 200. Additionally, in this modified example, the protrusions (the locking member side convex portion 46A and the engagement member side convex portion 43A) generating a sense of clicking are provided. However, it is needless to mention that the size and the shape of the protrusion are set to be sufficiently small to a degree that a force necessary for climbing over the protrusion at the time of generating a sense of clicking does not cause an unintended displacement of the other medical connector 200.

After the connectors are connected to each other, for example, the connectors are attached to a skin of a living body of a patient having an indwelling needle indwelled therein so that the female connector portion 201 and the locking member L2A are covered by an adhesive sheet such as a dressing film. Thus, an unintended separation of the connector may be reliably prevented by preventing the movement of the locking member L2A Further, since the plurality of claws 23aA are restored from the elastic deformation state by moving the locking member L2A in a direction moving away from the other medical connector 200 at the time of separating the connectors from each other, the locked state can be released. Then, since a repulsive force of the sealing portion 22aA formed to seal the outer surface 201a of the female connector portion 201 can be exerted in a direction in which the connectors are separated from each other when the locked state is released in this way, it is possible to obtain satisfactory operability for separating the connectors from each other. At that time, in this example, since the sealing portion 22aA includes the tapered surface 22a1A which increases in diameter toward the proximal end side, it is possible to effectively exert the repulsive force of the sealing portion 22aA.

In addition, also in this modified example, an unintended separation of the connector may be reliably prevented by prohibiting the releasing of the locking at the time of first completing the locking using the locking member L2A in such a manner that the protruding widths of the locking member side convex portion 46A and the engagement member side convex portion 43A are enlarged.

As described above, according to the medical connector 21A of this modified example, when the male connector portion 22A of the medical connector 21A is inserted into the female connector portion 201 of the other medical connector 200, the locking portion 24A (the locking member L2A) slides on the engagement portion 23A (the plurality of claws 23aA) and a locked state where the engagement portion 23A cannot be pulled out of the other medical connector 200 can be set by the locking portion 24A sliding in this way.

Thus, according to this modified example, it is possible to connect the connectors to each other just by inserting the male connector portion 22A into the female connector portion 201 of the other medical connector 200. Further, according to this modified example, since the engagement portion 23A can be set in the locked state by the sliding of the locking portion 24A, it is possible to connect the connectors to each other without climbing over a stepped portion of the other medical connector 200 by the engagement portion 23A. Thus, according to this modified example, it is possible to suppress an unintended displacement of the other medical connector 200 while ensuring the ease of a connection operation with respect to the other medical connector 200.

Further, in the medical connector 21A of this modified example, the engagement portion 23A includes the plurality of claws 23aA and the outer peripheral protrusions 50A formed at the outer peripheral surfaces of the plurality of claws 23aA and the locking portion 24A includes the cylinder wall 33A which surrounds the plurality of claws 23aA. Thus, according to this modified example, it is possible to obtain the above-described effect, that is, an effect capable of suppressing an unintended displacement of the other medical connector 200 while ensuring the ease of a connection operation with respect to the other medical connector 200 with a simple configuration.

Further, in the locking portion 24A of this modified example, when the male connector portion 22A is inserted into the female connector portion 201 of the other medical connector 200, the male connector portion 22A slides while coming into contact with the female connector portion 201 and the cylinder wall 33A presses the outer peripheral protrusions 50A to elastically deform the plurality of claws 23aA, so that a locked state where the plurality of claws 23aA cannot be pulled out of the other medical connector 200 is set. Thus, according to this modified example, since it is possible to connect the connectors to each other just by inserting the male connector portion 22A of the medical connector 21A into the female connector portion 201 of the other medical connector 200 while gripping the other medical connector 200 and the locking portion 24A of the medical connector 21A, it is possible to obtain satisfactory operability.

Further, in this modified example, the male connector portion 22A includes the sealing portion 22aA sealing the outer surface 201a of the female connector portion 201.

Thus, according to this modified example, it is possible to easily ensure the liquid-tightness at the time of connecting the connectors and to obtain satisfactory operability by the repulsive force of the sealing portion 22aA at the time of separating the connectors.

Further, in this embodiment, the cylinder wall 33A of the locking portion 24A includes the rotation regulation portion 33aA which prohibits the rotation of the female connector portion 201 of the other medical connector 200 relative to the cylinder wall 33A. Thus, according to this embodiment, it is possible to reliably maintain the locked state and the connection state.

Next, another modified example of the medical connector 21 described with reference to FIGS. 10A to 14B will be described in detail with reference to FIGS. 20A to 24B.

A medical connector 21B of this modified example is different from the medical connector 21A described with reference to FIGS. 15A to 19B in that a male connector portion 22B does not include a sealing portion sealing an outer surface of the female connector portion 201B and a rotation regulation portion 33aB prohibiting the rotation of the female connector portion 201B relative to a cylinder wall 33B has a different configuration, but the other points are the same as each other.

Figure 20A:
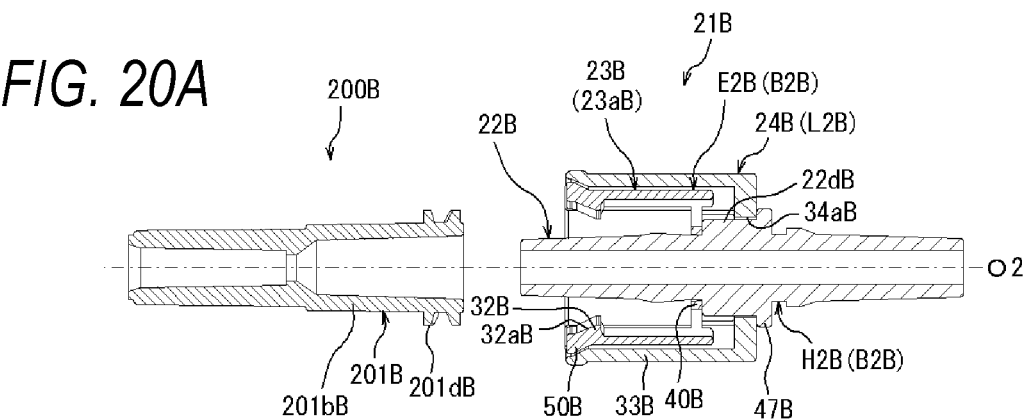
FIGS. 20A-20C illustrate a state at the time of the separation between another modified example of the medical connector illustrated in FIG. 10 and the other medical connector, where
Figure 20B:
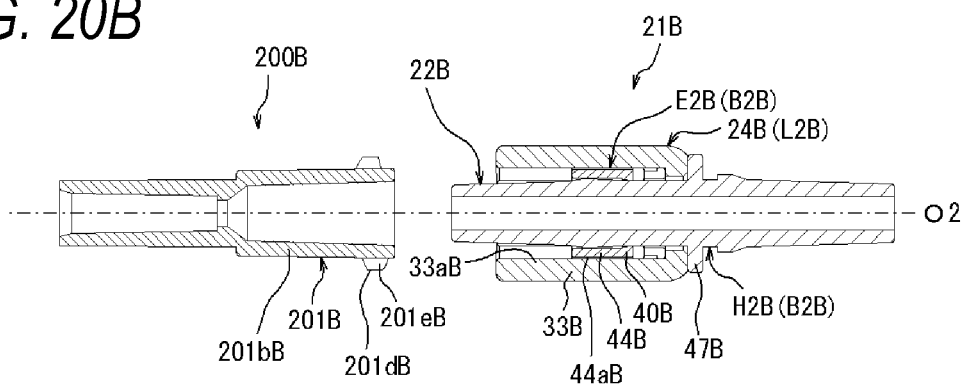
Figure 20C:
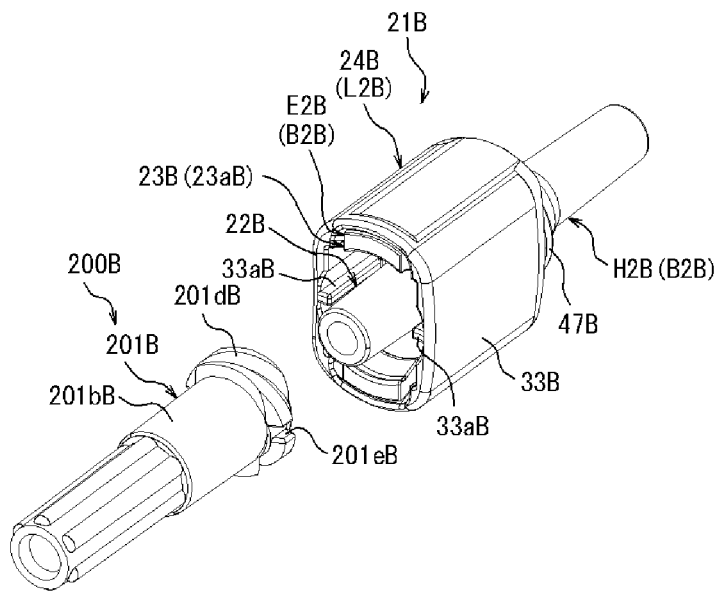

As illustrated in FIGS. 20A-20C, the medical connector 21B of this modified example is connectable to the other medical connector 200B in which a luer locking male screw portion 201dB is provided at an outer peripheral surface of a peripheral wall portion 201bB of the female connector portion 201B. That is, there is concern that the female connector portion 201B may be separated from the engagement protrusion 32B when the female connector portion 201B is freely rotatable relative to the cylinder wall 33B even when the engagement protrusions 32B of the plurality of claws 23aB are locked to such a male screw portion 201dB to enter the locked state.

For this reason, in this example, the male screw portion 201dB of the other medical connector 200B is provided with a pair of rotation prohibiting groove portions 201eB extending along the axis O2 and the inner peripheral surface of the cylinder wall 33B is provided with a rotation regulation portion 33aB formed as a pair of ridges engageable with the groove portions 201eB.

Figure 21:
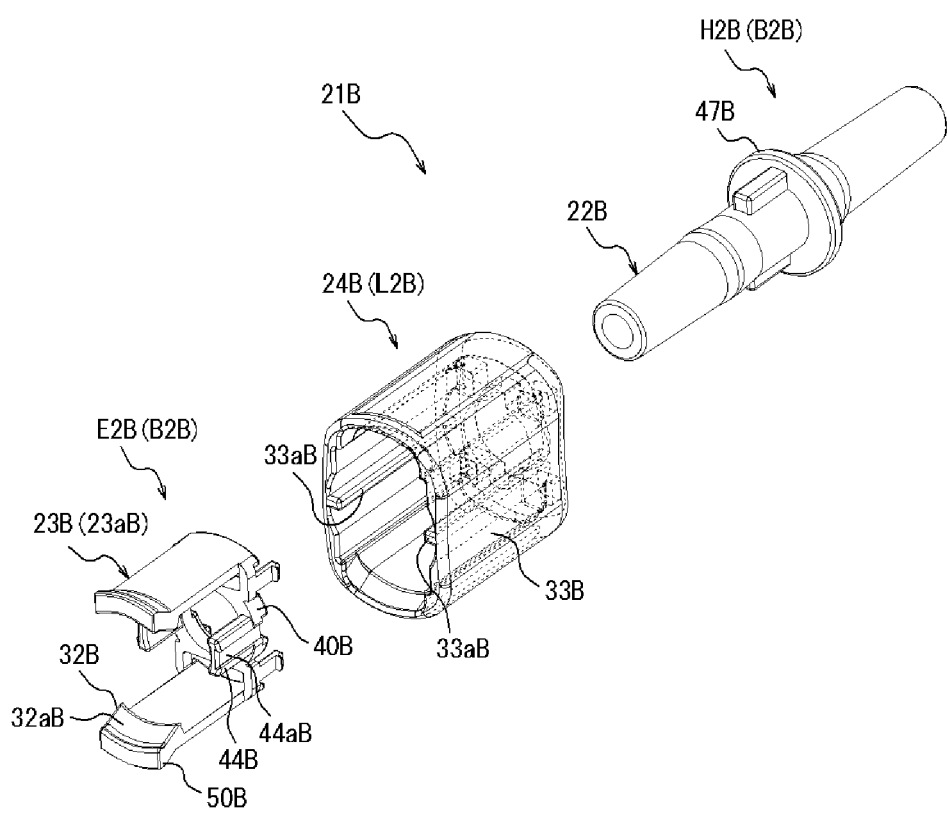
FIG. 21 is an exploded perspective view of the medical connector illustrated in FIG. 20.
Figure 22:
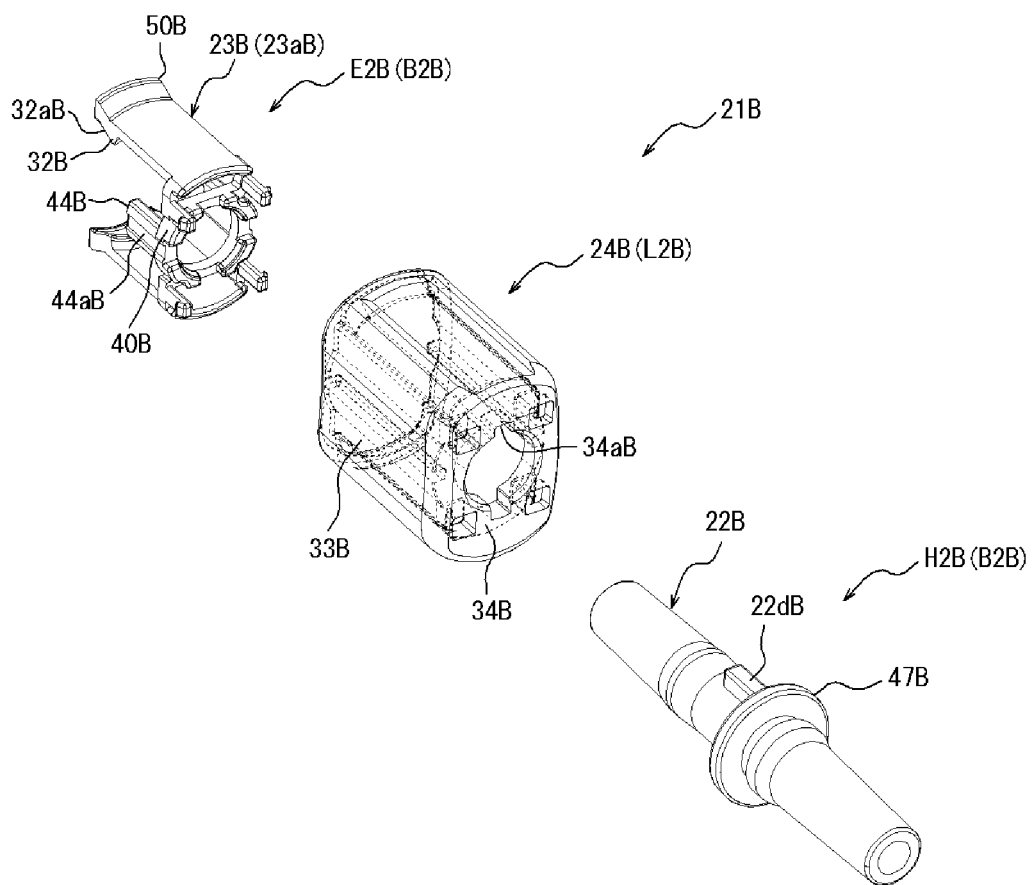
FIG. 22 is an exploded perspective view in which the medical connector illustrated in FIG. 20 is viewed from a different angle.

Furthermore, as illustrated in FIG. 21, a pair of guide pieces 44B provided at an engagement member E2B is provided with a guiding groove portion 44aB capable of guiding the rotation regulation portion 33aB. Further, as illustrated in FIG. 22, a proximal end side end portion of the cylinder wall 33B is provided with an inward flange 34B extending toward the inner peripheral side. The inward flange 34B is disposed in a slidable manner between a flange 47B provided at the proximal end portion of the male connector portion 22B of the housing H2B and a bottom wall 40B of the engagement member E2B retained by the male connector portion 22B. In addition, the inward flange 34B includes two grooves 34aB and the grooves 34aB engage with two ridges 22dB formed at the distal end side of the flange 47B of the male connector portion 22B, so that the locking member L2B is attached to the male connector portion 22B of the housing H2B to be slidable.

A method of connecting the medical connector 21B and the other medical connector 200B with the above-described configuration is as below.

Figure 23A:
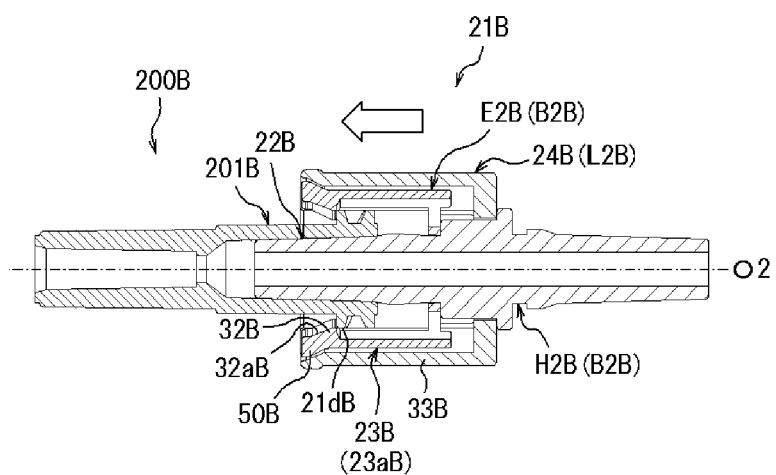
FIGS. 23A-23B illustrate a state at the time of starting the locking between the medical connector and the other medical connector illustrated in FIG. 20, where
Figure 23B:
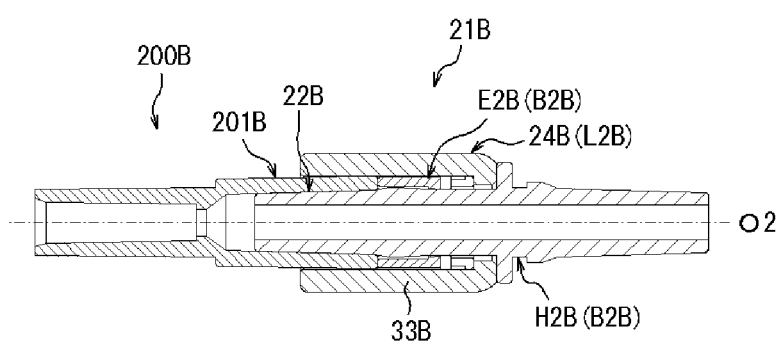

First, a groove portion 201eB provided at the male screw portion 201dB of the other medical connector 200B engages with the rotation regulation portion 33aB provided at the inner peripheral surface of the cylinder wall 33B of the locking member L2B, for example, while the other medical connector 200B is held by a left hand and the locking member L2B of the medical connector 21B is held by a right hand from a state where the medical connector 21B and the other medical connector 200B are separated from each other as illustrated in FIGS. 20A-20C. Then, when the locking member L2B is moved in a direction moving close to the other medical connector 200B so that the male connector portion 22B of the medical connector 21B is inserted into the female connector portion 201B of the other medical connector 200B, the outer peripheral surface of the male connector portion 22B comes into contact with the inner peripheral surface of the female connector portion 201B as illustrated in FIGS. 23A-23B.

At this time, since a gap between the engagement protrusions 32B of the plurality of claws 23aB (in this example, a distance between the portions facing each other with the axis O2 interposed therebetween) is larger than an outer diameter of the male screw portion 201dB of the female connector portion 201B, the male screw portion 201dB of the female connector portion 201B can climb over the engagement protrusions 32B of the plurality of claws 23aB of the engagement member E2B without climbing over the male screw portion 201dB of the female connector portion 201B by the plurality of claws 23aB. At that time, it is possible to smoothly guide the male screw portion 201dB of the female connector portion 201B between the plurality of claws 23aB by the tapered surfaces 32aB of the engagement protrusions 32B of the plurality of claws 23aB.

Figure 24A:
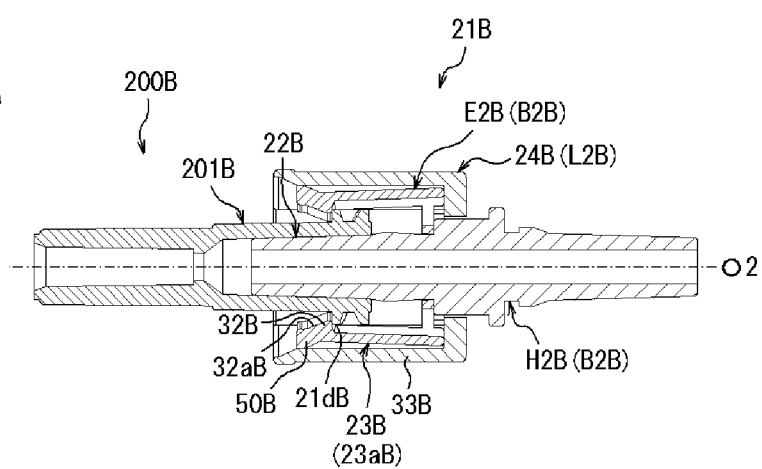
FIGS. 24A-24B illustrate a state at the time of completing the locking between the medical connector and the other medical connector illustrated in FIG. 20, where
Figure 24B:
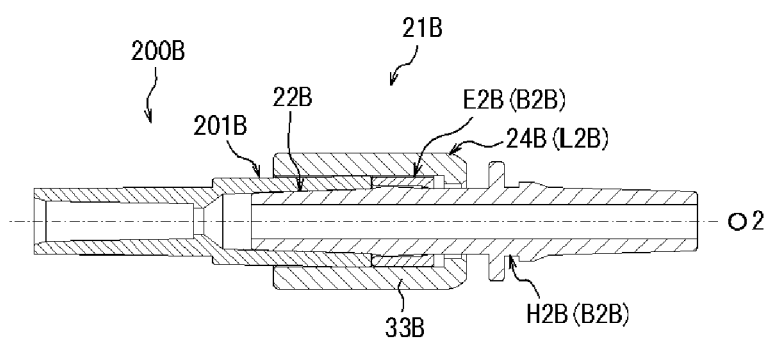

Then, when the locking member L2B is further moved in a direction of moving close to the other medical connector 200B, the connector body B2B (the housing H2B and the engagement member E2B) cannot move anymore and thus the locking member L2B slides on the engagement member E2B. For this reason, since the cylinder wall 33B presses the outer peripheral protrusions 50B of the plurality of claws 23aB of the engagement member E2B to elastically deform the plurality of claws 23aB, a locked state where the plurality of claws 23aB cannot be pulled out of the other medical connector 200B can be set as illustrated in FIGS. 24A-24B. Here, in this example, the locked state indicates a state where the engagement protrusions 32B of the plurality of claws 23aB are pressed by the cylinder wall 33B of the locking portion 24B (the locking member L2B) to be retained by the male screw portion 201dB of the female connector portion 201B. Further, in this example, a connection between the connectors is completed at a time point of the locked state.

Then, at this time, in this example, a relative rotation between the female connector portion 201B and the locking member L2B is prohibited by the engagement between the groove portion 201eB (see FIGS. 20A-20C) and the rotation regulation portion 33aB. Thus, according to this example, it is possible to reliably maintain the locked state and the connection state by prohibiting the rotation of the female connector portion 201B even when the medical connector 200B including the male screw portion 201dB is a connection target.

Figure 25:
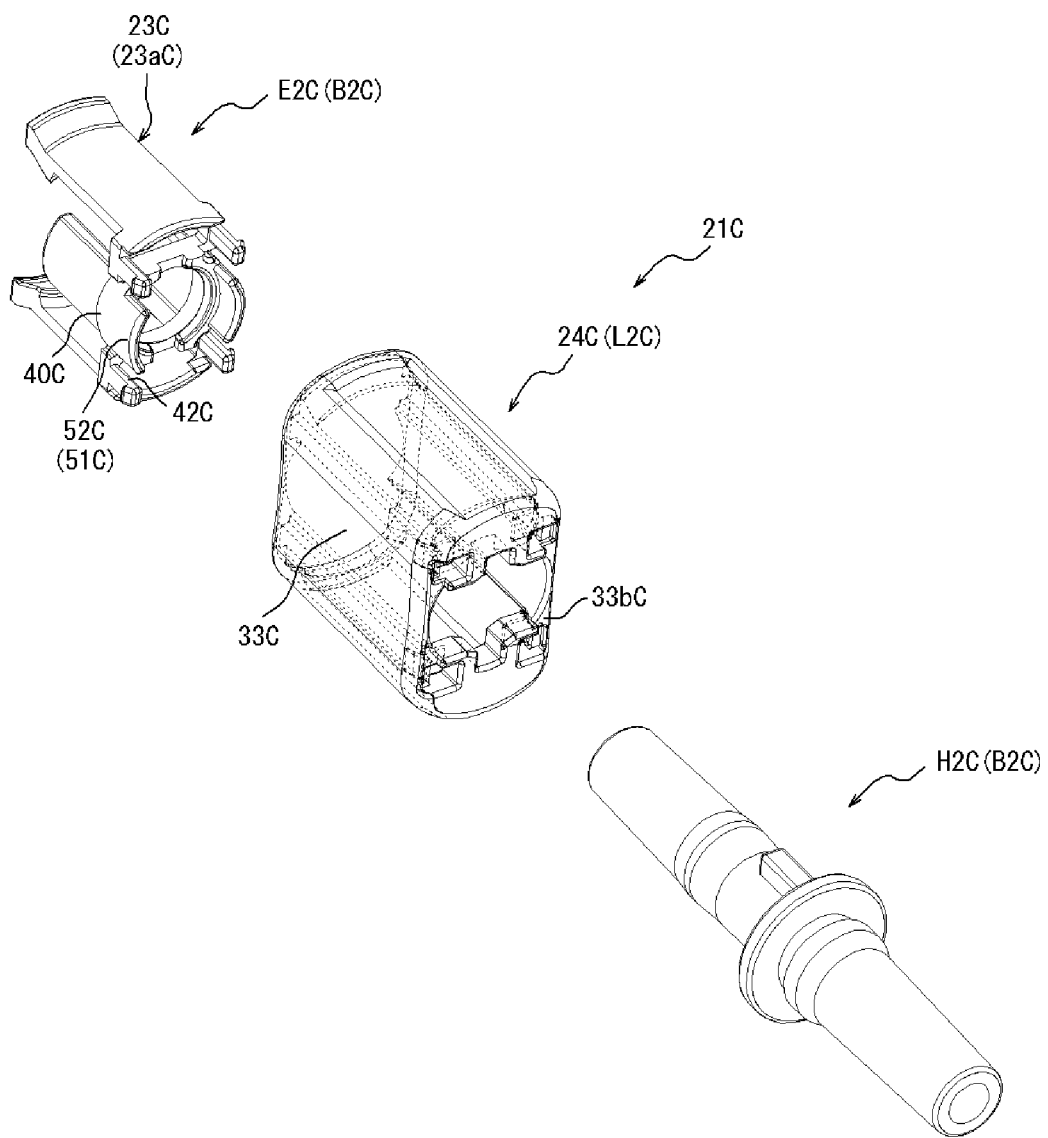
FIG. 25 is an exploded perspective view illustrating still another example of the medical connector illustrated in FIG. 10.
Figure 26A:
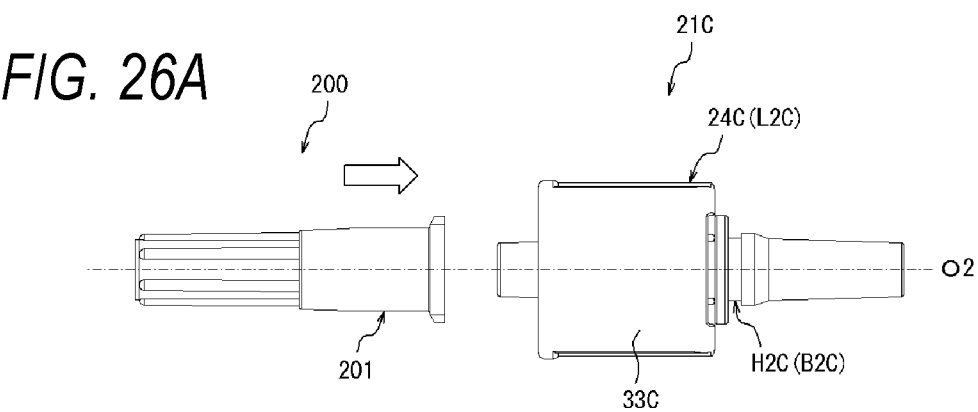
FIG. 26A-26B illustrate the medical connector illustrated in FIG. 25 along with the other medical connector, where
Figure 26B:
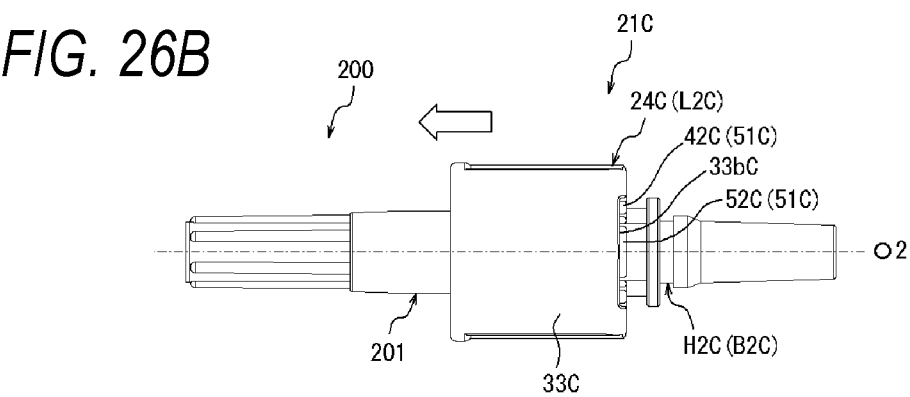

Next, still another modified example of the medical connector 21 described with reference to FIGS. 10A to 14B will be described in detail with reference to FIGS. 25 and 26A-26B.

The medical connector 21C of this modified example is different from the medical connector 21A described with reference to FIGS. 15A to 19B in that a male connector portion 22C does not include a sealing portion sealing the outer surface of the female connector portion 201 and an engagement member E2C includes a complete locking visual check portion 51C, but the other points are the same as each other.

As illustrated in FIGS. 20A-20C, in this modified example, a bottom wall 40C of the engagement member E2C is provided with a pair of protrusion pieces 52C which has a circular-arc cross-section and protrudes toward the proximal end side. As illustrated in FIG. 21, the pair of protrusion pieces 52C forms the complete locking visual check portion 51C which protrudes from the proximal end surface 33bC of the cylinder wall 33C toward the proximal end side so as to be visually recognized from the outside of the cylinder wall 33C in the radial direction when the locking portion 24C (the locking member L2C) slides so that the plurality of claws 23aC (the engagement portion 23C) are set to the locked state.

In addition, in this example, four protrusions 42C provided at the bottom wall 40B of the engagement member E2C also form such a complete locking visual check portion 51C. In this example, as illustrated in FIGS. 26A-26B, the pair of protrusion pieces 52C and four protrusions 42C are formed to protrude from the proximal end surface 33bC formed as a notched portion formed at the proximal end side of the cylinder wall 33C when the locking is completed and to be visible from the outside of the cylinder wall 33C in the radial direction.

As described above, the medical connector 21C of this modified example includes the complete locking visual check portion 51C which protrudes from the proximal end surface 33bC of the cylinder wall 33C toward the proximal end side and is visible from the outside of the cylinder wall 33C in the radial direction when the locking portion 24C slides so that the plurality of claws 23aC enter the locked state. Thus, according to this modified example, the operator can check whether the locking is completed by seeing the complete locking visual check portion 51C.

The above-described configurations merely illustrate an embodiment of the invention and can be modified into various forms within the scope of claims. For example, in the above-described embodiment, each of the connector bodies B1, B2, B2A, B2B, and B2C includes two members, but may include one member or three or more members. Further, each of the locking members L1, L2, L2A, L2B, and L2C may include two or more members. Further, each of the claws 3a, 23a, 23aA, 23aB, and 23aC of the engagement portions 3, 23, 23A, 23B, and 23C is not limited to two members and may be three or more members.

Further, in the above-described embodiment, the fitting wall side fitting portion 7a is formed as the opening portion and the cylinder wall side fitting portion 17 is formed as the claw including the fitting protrusion 17a. On the contrary, the fitting wall side fitting portion 7a may be formed as the claw including the fitting protrusion and the cylinder wall side fitting portion 17 may be formed as the opening portion. In that case, the operation portion 18 can be provided at the fitting wall 7. Further, a concave portion to which the fitting protrusion is fitted may be used instead of the opening portion serving as the fitting wall side fitting portion 7a or the cylinder wall side fitting portion 17.

Further, in the embodiment described with reference to FIGS. 1A to 9B, the cylinder wall 13 may be provided with, for example, the rotation regulation portion 33a illustrated in FIGS. 10A-10C or the rotation regulation portion 33aB illustrated in FIGS. 20A-20C to more reliably maintain the locked state and the connection state. Further, in the embodiment described with reference to FIGS. 1A to 9B, the male connector portion 2 may be provided with the sealing portion 22aA illustrated in FIGS. 15A-15C to easily ensure the liquid-tightness.

Further, in the above-described embodiment, a case has been described in which a gap between the engagement protrusions 12, 32, and 32A of the plurality of claws 3a, 23a, 23aA, and 23aB is set to a size which does not need to climb over the stepped portions of the other medical connectors 100, 200, and 200B by the plurality of claws 3a, 23a, 23aA, and 23aB at the time of setting a state where the plurality of claws 3a, 23a, 23aA, and 23aB cannot be pulled out of the other medical connectors 100, 200, and 200B, but the invention is not essentially limited thereto. For example, a gap between the engagement protrusions 12, 32, and 32A of the plurality of claws 3a, 23a, 23aA, and 23aB may be set to a size which causes such climbing if a force necessary for such climbing is sufficiently small to a degree that an unintended displacement of each of the other medical connectors 100, 200, and 200B does not occur.

REFERENCE NUMERAL LIST 1 medical connector
2 male connector portion
2a proximal end portion of male connector portion
3 engagement portion
3a claw
4 locking portion
5 female connector portion
6 mixed injection port portion
6a valve body
7 fitting wall
7a fitting wall side fitting portion
8 protrusion
8a protrusion
9 concave portion
10 proximal flange
10a tapered surface
11 plate piece
12 engagement protrusion
12a tapered surface
13 cylinder wall
14 protrusion
14a insertion hole
14b protrusion
15 groove portion
16 distal flange
16a tapered surface
17 cylinder wall side fitting portion
17a fitting protrusion
18 operation portion
19 locking protrusion
19a tapered surface
21 medical connector
22 male connector portion
23 engagement portion
23a claw
24 locking portion
25 connection portion
31 plate piece
32 engagement protrusion
32a tapered surface
33 cylinder wall
33a rotation regulation portion
34 protrusion
39 tapered surface
40 bottom wall 41 penetration hole
42 protrusion
43 engagement member side convex portion
44 guide piece
45 opening portion
46 locking member side convex portion
47 flange
48 annular convex portion
49 convex portion
50 outer peripheral protrusion
50a tapered surface
21A medical connector
22A male connector portion
22aA sealing portion
22a1A tapered surface
22a2A sealing flange
22bA annular concave portion
22cA groove portion
23A engagement portion
23aA claw
24A locking portion
25A connection portion
31A plate piece
32A engagement protrusion
32aA tapered surface
33A cylinder wall
33aA rotation regulation portion
34A protrusion
34aA protrusion
39A tapered surface
40A bottom wall
41A penetration hole
42A protrusion
43A engagement member side convex portion
44A guide piece
45A opening portion
46A locking member side convex portion
47A flange
49A convex portion
50A outer peripheral protrusion
50aA tapered surface
21B medical connector
22B male connector portion
22dB ridge
23B engagement portion
23aB claw
24B locking portion
32B engagement protrusion
32aB tapered surface
33B cylinder wall
33aB rotation regulation portion
34B inward flange
34aB groove
40B bottom wall
44B guide piece
44aB guiding groove portion
47B flange
50B outer peripheral protrusion
21C medical connector
22C male connector portion
23C engagement portion
23aC claw
33C cylinder wall
33bC proximal end surface
40C bottom wall
42C protrusion
51C complete locking visual check portion
52C protrusion piece
100 other medical connector
101 female connector portion
101a outer surface portion
101b peripheral wall portion
102 male connector portion
103 female connector side housing
104 male connector side housing
105 valve body
105a outer surface portion
106 engagement concave portion
200 other medical connector
201 female connector portion
201a outer surface
201b peripheral wall portion
201c inner peripheral surface
207 engagement convex portion
200B other medical connector
201B female connector portion
201bB peripheral wall portion
201dB male screw portion
201eB groove portion
O1, O2 axis
H1, H2, H2A, H2B, H2C housing
E1, E2, E2A, E2B, E2C engagement member
L1, L2, L2A, L2B, L2C locking member
B1, B2, B2A, B2B, B2C connector body
S2A sealing member

What is claimed is:

1. A medical connector configured to be connected to another medical connector, the medical connector comprising:
   a housing comprising a male connector portion, the male connector portion comprising a plurality of concave portions located at a proximal end portion of the male connector portion;
   an engagement portion that extends at least partially around the male connector portion such that the engagement portion and the male connector portion overlap in an axial direction of the medical connector, the engagement portion comprising:
      a plurality of claws, and
      a fitting wall that is connected to proximal end portions of the plurality of claws, the fitting wall comprising a plurality of protrusions located on a proximal end portion of the fitting wall and fitted to respective ones of the concave portions of the male connector portion so as to fix the engagement portion to the housing; and
   a locking portion configured to slide on the engagement portion to set a locked state in which the engagement portion is inhibited from being pulled out of the other medical connector when the male connector portion is inserted into a female connector portion of the other medical connector;
   wherein, when the male connector portion is inserted into the female connector portion of the other medical connector, the locking portion is slidable relative to the male connector portion.

2. The medical connector according to claim 1, wherein the locking portion comprises:
   a cylinder wall that surrounds the plurality of claws, and
   a locking protrusion that is formed at an inner peripheral surface of the cylinder wall.

3. The medical connector according to claim 2, wherein, when the male connector portion is inserted into the female connector portion of the other medical connector, the cylinder wall slides while being pressed by the other medical connector and the locking protrusion presses the plurality of claws to elastically deform the claws, such that the locking portion sets the locked state in which the plurality of claws are inhibited from being pulled out of the other medical connector.

4. The medical connector according to claim 2,
wherein the fitting wall comprises a fitting wall side fitting portion; and
wherein the cylinder wall comprises a cylinder wall side fitting portion, and
wherein the fitting wall side fitting portion and the cylinder wall side fitting portion are fitted to each other to prevent the cylinder wall from sliding toward the other medical connector when the cylinder wall sets the plurality of claws in the locked state.

5. The medical connector according to claim 4,
wherein the cylinder wall comprises an operation portion formed at an outer peripheral surface of the cylinder wall, and
wherein, when the operation portion is pressed, fitting between the fitting wall side fitting portion and the cylinder wall side fitting portion is released.

6. The medical connector according to claim 2,
wherein the cylinder wall of the locking portion comprises a rotation regulation portion that prohibits a rotation of the female connector portion of the other medical connector relative to the cylinder wall.

7. The medical connector according to claim 1,
wherein the engagement portion further comprises:
    a plurality of outer peripheral protrusions that are formed at outer peripheral surfaces of the plurality of claws, and
wherein the locking portion includes a cylinder wall which surrounds the plurality of claws.

8. The medical connector according to claim 7,
wherein, when the male connector portion is inserted into the female connector portion of the other medical connector, the male connector portion slides while coming into contact with the female connector portion and the cylinder wall presses the outer peripheral protrusions to elastically deform the plurality of claws, such that the locking portion sets the locked state in which the plurality of claws are inhibited from being pulled out of the other medical connector.

9. The medical connector according to claim 7, further comprising:
    a complete locking visual check portion that protrudes from a proximal end surface of the cylinder wall toward a proximal end side and is visible from the outside of the cylinder wall in a radial direction when the locking portion slides such that the plurality of claws are set to the locked state.

10. The medical connector according to claim 5,
wherein the male connector portion comprises a sealing portion that seals an outer surface of the female connector portion.

11. A method of using a first connector and a second connector, the method comprising:
    providing a first connector comprising:
        a housing comprising a male connector portion, the male connector portion comprising a plurality of concave portions located at a proximal end portion of the male connector portion,
        an engagement portion that extends at least partially around the male connector portion such that the engagement portion and the male connector portion overlap in an axial direction of the medical connector, the engagement portion comprising:
            a plurality of claws, and
            a fitting wall that is connected to proximal end portions of the plurality of claws, the fitting wall comprising a plurality of protrusions located on a proximal end portion of the fitting wall and fitted to respective ones of the concave portions of the male connector portion so as to fix the engagement portion to the housing,
        a locking portion comprising a cylinder wall surrounding the plurality of claws, and a locking protrusion formed at an inner peripheral surface of the cylinder wall;
    providing a second connector comprising a female connector portion;
    inserting the male connector portion of the first connector into the female connector portion of the second connector;
    sliding the cylinder wall on the engagement portion, wherein, when the male connector portion of the first connector is inserted into the female connector portion of the second connector, the locking portion is slidable relative to the male connector portion; and
    setting the first connector and the second connector in a locked state when the locking protrusion presses the plurality of claws to elastically deform the claws.

12. A method of using a first connector and a second connector, the method comprising:
    providing a first connector comprising:
        a housing comprising a male connector portion, the male connector portion comprising a plurality of concave portions located at a proximal end portion of the male connector portion,
        an engagement portion that extends at least partially around the male connector portion such that the engagement portion and the male connector portion overlap in an axial direction of the medical connector, the engagement portion comprising:
            a plurality of claws,
            a plurality of outer peripheral protrusions formed at outer peripheral surfaces of the plurality of claws, and
            a fitting wall that is connected to proximal end portions of the plurality of claws, the fitting wall comprising a plurality of protrusions located on a proximal end portion of the fitting wall and fitted to respective ones of the concave portions of the male connector portion so as to fix the engagement portion to the housing,
        a locking portion comprising a cylinder wall surrounding the plurality of claws;
    providing a second connector comprising a female connector portion;
    inserting the male connector portion of the first connector into the female connector portion of the second connector;
    sliding the cylinder wall on the engagement portion, wherein, when the male connector portion of the first connector is inserted into the female connector portion of the second connector, the locking portion is slidable relative to the male connector portion; and
    setting the first connector and the second connector in a locked state when the cylinder wall presses the outer peripheral protrusions to elastically deform the plurality of claws.

* * * * *